United States Patent [19]
Rabbani et al.

[11] Patent Number: 5,998,135
[45] Date of Patent: Dec. 7, 1999

[54] ENERGY TRANSFER HYBRIDIZATION ASSAY USING INTERCALATORS AND LANTHANIDE METALS

[75] Inventors: Elazar Rabbani, New York; Ian Hurley, Staten Island, both of N.Y.

[73] Assignee: Enzo Diagnostics, Inc., Farmingdale, N.Y.

[21] Appl. No.: 08/486,053

[22] Filed: Jun. 7, 1995

Related U.S. Application Data

[63] Continuation of application No. 08/194,215, Feb. 9, 1994, abandoned, which is a continuation of application No. 07/314,995, Feb. 24, 1989, abandoned.

[51] Int. Cl.$^6$ ............................. C12Q 1/68; C07H 21/04
[52] U.S. Cl. .............................................. 435/6; 536/24.3
[58] Field of Search ............................. 435/6, 91.1, 810, 435/287, 291; 935/16, 77, 78; 422/55, 57, 61; 536/24.3

[56] References Cited

U.S. PATENT DOCUMENTS

| | | |
|---|---|---|
| 4,257,774 | 3/1981 | Richardson et al. . |
| 4,547,569 | 10/1985 | Letsinger et al. . |
| 4,563,417 | 1/1986 | Albarella et al. . |
| 4,582,789 | 4/1986 | Sheldon, III et al. . |
| 4,637,988 | 1/1987 | Hinshaw et al. . |
| 4,670,572 | 6/1987 | Hinshaw et al. . |
| 4,707,352 | 11/1987 | Stavrianopoulos . |
| 4,707,440 | 11/1987 | Stavrianopoulos . |
| 4,711,955 | 12/1987 | Ward et al. . |
| 4,868,103 | 9/1989 | Stavrianopoulos et al. ................ 435/5 |
| 4,921,805 | 5/1990 | Gebeyehu et al. ...................... 435/270 |

FOREIGN PATENT DOCUMENTS

| | | |
|---|---|---|
| 070685A2 | 7/1982 | European Pat. Off. . |
| 144914A3 | 11/1984 | European Pat. Off. . |
| 242527B1 | 5/1992 | European Pat. Off. . |
| 285057B1 | 3/1995 | European Pat. Off. . |
| 8707955 | 6/1987 | WIPO . |

OTHER PUBLICATIONS

Hemmilia, "Fluoroimmunoassays and Immunofluorometric Assays", *Clin. Chem.* 31(3):359–380 (1985).

Gibson P.E., et al., "Detection of Human Polyomavirus DNA in Urine Specimens by Hybridot Assay," *Arch. of Virol.* 84:233–240 (1985).

Soini, E. and Kojola, H., "Time–Resolved Fluorometer for Lanthanide Chelates, A New Generation of Nonisotopic Immunoassays, "*Clin. Chem.* 29(1):65–68 (1983).

Chan et al., *Abst. of the Fifth Intl. Symposium on Rapid Methods & Automation in Microbiology and Immunology*, Florence, Nov. 1987, p. 153.

Syvanen et al., "Time–resolved fluorometry: a sensitive method to quantify DNA–hybrids, "*Nucleic Acids Research* 14(2): 1017–1028 (1986).

Dahlen et al., "Sensitive detection of genes by sandwich hybridization and time–resolved fluorometry, "*Molecular & Cellular Probes 1:* 159–168 (1987).

Kubota et al., "Fluorescence Decay And Quantum Yield Characteristics of Acridine Orange And Proflavine Bound to DNA, "*Biophysical Chemistry*6:279–289 (1977).

Genest et al., "Investigation of DNA dynamics and drug–DNA interaction by steady state fluorescence anisotropy, "*Nucleic Acid Research*13:2603–2615 (1985).

Asseline et al., "Oligodeoxynucleotides covalently linked to intercalating dyes as base sequence–specific ligands. Influence of dye attachment site, "*The EMBO Journal.* 3(4):795–800 (1984).

Wakelin & Waring, , "The Unwinding of circular Deozyribonucleic Acid by Phenanthurinium Drugs: Structure–Activity Relations for the Intercalation Reaction", *Mol. Pharm.*9:544–561 (1974).

Wakelin & Waring, "Kinetics of Drug–DNA Interaction, "*J. Mol. Biol. 144*:183–214 (1980).

Saenger W., *Principles of Nucleic Acid Structure*, pp. 116–58 Springer–Verlag, New York.

Syvanen, "Nucleic Acid Hybridization: From Research Tool To Routine Diagnostic Method, "*Medical Biology* 64:313–324 (1986).

Syvanen et al., "Fast quantification of nucleic acid hybrids by affinity–based hybrid collection, "*Nucleic Acids Research* 14(12):5037–5048 (1986).

Sommer, R. and Tautz, D., "Minimal homology requirements for PCR primers, "*Nucleic Acids Research* 17(16):6749 (1989).

Georghiou, "Interaction of Acridine Drugs With DNA And Nucleotides," *Photochemistry and Photobiology 26:*59–68, Pergamon Press, Great Britain (1977).

(List continued on next page.)

*Primary Examiner*—Kenneth R. Horlick
*Attorney, Agent, or Firm*—Ronald C. Fedus, Esq.

[57] ABSTRACT

Disclosed is a nucleic acid hybridization assay composition for detecting the presence of absence of a target oligo- or polynucleotide in a sample. The composition comprises: a solid matrix having at least one surface which is substituted with a first intercalator capable of binding dsDNA dsRNA, or DAN-RNA hybrids; a second intercalator, which may or may not comprise at least one fluorophore, said intercalator or said fluorophore each acting as either an energy donor or an energy acceptor; and an oligo- or polynucleotide probe which is specifically hybridizable with the target oligo- or polynucleotide and has directly or indirectly bound thereto, at least one lanthanide metal chelate or at least one fluorophore, each acting as either an energy donor or an energy acceptor. Also disclosed are a method and kit for its use.

53 Claims, No Drawings

OTHER PUBLICATIONS

Oser A. et al., "Sensitive non–radioactive dot–blot hybridization using DNA probes labelled with chelate group substituted psoralen and quantitative detection by europium ion fluorescence," *Nuc. Acid Research 16(3)*:1181–1197 (1988).

Horrocks, W.D., et al., "Laser–Induced Lanthanide Ion Luminescence Lifetime Measurements by Direct Excitation of Metal Ion Levels, A New Class of Structural Probe for Calcium–Binding Proteins and Nucleic Acids," *Journal of the American Chem. Society 99(7)*:2378–2380 (1977).

Chun, P.K., et al., International Symposium on Rapid Methods and Automation in Microbiology and Immunology (5th, 1987, Florence, Italy) published in *Rapid Methods and Automation in Microbiology and Immunology,* Balows, A., et al., Eds., Brixia Academic Press Brescia, pp. 572–577 (1989).

Saeger, W., *Principles of Nucleic Acid Structure,* Springer–Verlag, New York, 1984, pp. 116–158.

*Nucleic Acids Research,* vol. 17, No. 16, Sommer and Tautz, "Minimal Requirements for PCR primers", p. 6749, 1989.

ENERGY TRANSFER HYBRIDIZATION ASSAY USING INTERCALATORS AND LANTHANIDE METALS

This is a continuation of application Ser. No. 08/194,215, filed on Feb. 9, 1994, abandoned, which is a continuation of application Ser. No. 07/314,995, filed Feb. 24, 1989, abandoned.

BACKGROUND OF THE INVENTION

1) Field of the Invention

The present invention relates to the field of hybridization assay methods, and more particularly, it relates to hybridization assay techniques in which the presence of an analyte is determined by means of energy transfer.

2) Brief Description of the Prior Art

Nucleic acid hybridization is an effective method for detecting and identifying pathogenic organisms and genetic disorders. It is also useful for mapping genes on chromosomes and in general has a wide spectrum of applications in clinical research. But despite the commercial availability of numerous target specific polynucleotide probes, detection or identification of infectious agents by hybridization is often not the preferred method. Instead, infectious agents are still cultured and identified by laborious, subjective and frequently inaccurate procedures.

Some of the commonly cited reasons for not using hybridization assays are the relative complexity of performing the assay procedure and the lack of sufficient sensitivity for detection or quantification when small numbers of the target organism are present. The most sensitive hybridization assays depend upon the use of radioisotopes for labeling the nucleic acid probe. However, the use of radioisotopes necessitates safety precautions and elaborate means for their disposal. In addition, radiolabels often have a short half-life (e.g., the half-life of $^{32}P$ is fourteen days), which makes their use expensive. Thus, it is recognized as being highly desirable to develop and improve nonisotopic hybridization detection methods.

At present, alternative methods are available which depend, inter alia, either on the development of color or on the emission of fluorescence. Recently, highly sensitive time-resolved fluorescence (TRF) labeling, based on the long-lived emissions of lanthanide chelates, has been used in immunoassay and immunological detection of hybridization assay probes. Even though lanthanide ions, such as europium ($Eu^{+3}$) and terbium ($Tb^{+3}$) exhibit extremely weak luminescence when they are directly excited by visible light, it has been shown that these ions become highly fluorescent when they are chelated by organic ligands with good energy absorption properties. Absorption of the light by the ligand is followed by an efficient energy transfer from the excited ligand to the energy levels of the lanthanide ions. The fluorescence of lanthanide chelates is characterized by broad excitation in the absorption region of the ligand, a large Stokes' shift (>250 nm), narrow emission lines typical of the metal and an exceptionally long fluorescence lifetime (100–1000 usec). See, Horrocks, W. D. et al., "Laser-Induced Lanthanide Ion Luminescence Lifetime Measurements by Direct Excitation of Metal Ion Levels, A New Class of Structural Probe for Calcium-Binding Proteins and Nucleic Acids," *Journal of the American Chemical Society* 99(7):2378–2380 (1977) and Hemmilia, Clin. Chem., 31:359–370(1985).

In TRF assays, signals at the emission wavelengths of the lanthanide chelates are measured after a lapse in time between excitation and emission. This time-lag is sufficiently long to ensure that the specific long-lived fluorescence emissions of the lanthanide chelates are detected, but that the short-lived (<1 usec) background resulting from the intrinsic fluorescence of biological materials and other assay components (a serious problem in fluorometric measurements in biological samples) is not measured. This results in higher signal-to-noise ratios than are commonly observed in conventional fluorescence assays and consequently in an improvement in assay sensitivity.

Typically, TRF immunoassays are performed using $Eu^{+3}$ linked to antibodies via covalently bound chelators. After formation of the complex between the antigen and the antibody-chelate $Eu^{+3}$, the $Eu^{+3}$ in the complex is released, bound to suitable chelators such as those referred to above, then trapped in micelles. Pulsed light with an appropriate wavelength is applied to this micelle system. The resulting fluorescence is measured using a time resolving fluorometer. Under optimal conditions (i.e., high quality antibodies, stable chelation complexes, and suitable time resolving fluorometers), TRF immunoassays have the potential to exceed sensitivity levels obtainable with radioisotopic labels. See, Gibson, et al., Arch. of Virol., 84:233(1985).

TRF immunoassays with sensitivity levels comparable to radioimmunoassay using $^{125}I$ labels have been successfully used to measure levels of peptide hormones, alpha-fetoprotein, thyrotropin, choriogonadotropin and influenza viruses in clinical specimens. See, Hemmilia, supra; Soini and Kojola, Clin. Chem., 29:65(1983); Chun, P. K. et al., "Rapid Detection of Antigens Using Colloidal Gold in Membrane Based Immunoassays," from International Symposium on Rapid Methods and Automation in Microbiology and Immunology (5th) 1987, Florence, Italy, published in *Rapid Methods and Automation in Microbiology and Immunology*, Balows, A. et al., Editors, Brixia Academic Press, Brescia, pages 572–577 (1989).

Syvanen, et al., Nuc. Ac. Res. 14:1017(1986) have applied the technique of TRF immunoassays to the detection of DNA hybrids formed in sandwich hybridization assays. DNA probes carrying haptenic sulfone groups were hybridized to nitrocellulose-bound target DNA sequences (adenovirus genomic DNA). The hybrids were detected using a two-step antibody system. The first antibodies specifically recognized and became bound to the sulfone labels on the probe. The second antibodies consisted of sheep anti-rabbit IgG labeled with $Eu^{+3}$ by chelation. The $Eu^{+3}$ was released from this complex, chelated to diketones, trapped in micelles, and excited with UV light. The resulting emission was detected using a time resolving fluorometer. Syvanen et al state that $Eu^{+3}$ can be bound to organic molecules by mediation of EDTA derivatives and that these chelates are unstable at hybridization conditions (data not shown), and that is the reason why the probe DNA cannot be directly labelled with Eu-EDTA chelates.

Two additional solid phase sandwich hybridization assays which employ TRF detection of hybridized probes and which are similar to the method described by Syvanen, et al., have been reported. Dahlen, et al., used streptavidin-$Eu^{+3}$, with the $Eu^{+3}$ attached to streptavidin through a diethylenetriamine pentaacetic acid (DTPA) chelator, to detect biotinylated probes in matrix-bound hybridization complexes. Dahlen, et al., Mol. & Cell. Probes 1:159(1987). In the sandwich assay developed by Oser, et al., DTPA was attached to poly-L-lysine groups which were covalently bound to probe DNA via psoralen linkages. The probes were labeled with $Eu^{+3}$ following hybridization. Nitrocellulose was used as the matrix in this system. Oser. et al., Nuc. Ac. Res., 16:1181(1988).

In both of these assays, as well as in the Syvanen, et al., assay, $Eu^{+3}$ was measured by TRF following its release from the hybridization-detection complex. Notwithstanding the high sensitivity of these reported TRF-DNA hybridization assays, the length and complexity of these procedures make them unattractive for use in clinical laboratory settings. In addition, the lower detection levels of these assays are limited by high backgrounds resulting from the presence of measurable quantities of $Eu^{+3}$ in assay reagents, as well as in the environment (i.e., dust).

In another approach Sheldon III, et al., in U.S. Pat. No. 4,582,789, disclose a process for labeling nucleic acids with psoralen derivatives, which are also intercalators. A spacer arm chemically links the alkylating intercalation moiety with the label moiety, thereby allowing the label to react without interference, with detection means, such as antibodies.

Letsinger et al., U.S. Ser. No. 444,438, filed Nov. 24, 1982, now abandoned is said by Sheldon et al., supra, to disclose bifunctional intercalators containing a phenanthridinium moiety as an agent for introducing markers (e.g., fluorescent probes) at specified regions in polynucleotides.

Albarella et al, in the European Publication 0,144,914 and in the U.S. Pat. No. 4,563,417 disclose a method of detecting a polynucleotide sequence, which is based, a priori, on a conventional antigen-antibody system. This method requires the formation of two complexes, the formation of a polynucleotide/polynucleotide complex, and the formation of an antigen/antibody complex. The target sequence is detected by means of an interaction between two labels. The preferred labeling pair is a pair of enzymes which interact sequentially to produce a detectable product. Another labeling pair which is disclosed, is one that involves energy interactions such as between a fluorescer or luminescer and a quencher for the photo-emission of the first label. Where the absorbing label is also a fluorescer, a second emission is the detectable signal.

Heller, et al in European Publication 0,070,685, published on Jan. 26, 1983, disclose a homogenous assay in which two single-stranded polynucleotide probes that are complementary to mutually exclusive portions of the target polynucleotide, are used. In one embodiment of the assay, the first probe has an absorber/emitter moiety which absorbs a shorter wavelength of light than the absorber/emitter moiety on the second probe, but emits light in a wavelength region that overlaps with the absorbance region of absorber/emitter moiety on the second probe. The absorber/emitter moieties used are combinations of fluorescent compounds, such as derivatives of fluorescein and rhodamine.

Use of a complex of lanthanide metal and a chelating agent comprising a nucleus which is a triplet sensitizer is disclosed by Hinshaw et al., U.S. Pat. Nos. 4,637,988 and 4,670,572.

Wieder and Hale, in PCT Pub. No. WO87/07955 (filed Jun. 15, 1987), disclose a homogeneous assay which uses energy transfer as a means of detecting an analyte in very dilute solutions.

Stavrianopoulos et al., in European Publication No. 0242527 (published Oct. 28, 1987 and assigned to the instant assignee), disclose a homogeneous assay in which an energy transfer system for detection of the analyte is utilized. The energy donor or the energy acceptor can be either a fluorescent aromatic agent or a lanthanide metal. EP 0 242 527 is based upon the priority document, U.S. application Ser. No. 831,250, filed on Feb. 19, 1986, which issued as U.S. Pat. No. 4,868,103 on Sep. 19, 1989.

SUMMARY OF THE INVENTION

The present invention provides a nucleic acid hybridization assay composition for detecting the presence or absence of a target oligo- or polynucleotide in a sample. The composition comprises: a solid matrix having at least one surface which is substituted with a first intercalator capable of binding dsDNA, dsRNA or DNA-RNA hybrids, a second intercalator, which may or may not comprise at least one flurophore, said second intercalator or said flurophore, each acting as either an energy donor or an energy acceptor: and an oligo- or polynucleotide probe which is specifically hybridizable with the target oligo- or polynucleotide and has directly or indirectly bound thereto at least one lanthanide metal chelate or at least one fluorophore, each acting as either energy donor or an energy acceptor.

The invention further provides a nucleic acid hybridization assay method for detecting the presence or absence of a target oligo- or polynucleotide In a sample. This method begins by contacting a sample suspected of containing the target of interest with an oligo- or polynucleotide which is specifically hybridizable with the target and has directly or indirectly bound thereto at least one lanthanide metal chelate or at least one fluorophore, each acting as either an energy donor or an energy acceptor; permitting hybridization of the target and the oligo- or polynucleotide which is specifically hybridizable therewith to form a complex; contacting the complex with (i) a solid matrix having at least one surface which is substituted with a first intercalator capable of binding dsDNA, dsRNA or DNA-RNA hybrids and (ii) a second intercalator, which may or may not comprise at least one fluorophore, said second intercalator or said fluorophore, each acting as either an energy donor or an energy acceptor; and detecting any energy emitted from the energy donor.

The invention also provides a nucleic acid hybridization assay kit comprising, in packaged combination, reagents for detecting the presence or absence of a target oligo- or polynucleotide in a sample.

The present invention offers a number of significant advantages over previously available methods. The use of the intercalator-bound solid matrix of the invention which serves to capture and concentrate the duplexes formed between the target polynucleotide and the probe allows hybridization to proceed in liquid. Formation of nucleic acid hybrids, whether DNA/DNA, RNA/RNA or RNA/DNA, proceeds with significantly more rapid rates when both interacting species are present in solution, as opposed to one species being attached to a solid matrix.

Also, because the detection complex is on a surface, it is more completely and precisely localized than it would be if it were in solution and therefore, the signal that is generated can be made much stronger by increasing the photon density of each laser pulse through focusing the laser beam onto the appropriate spot. The increased photon density increases the chance of exciting each donor molecule. This increase in the number of exited donors per pulse increases the chance that the acceptor will be excited in its turn and give off a photon to be detected.

In one embodiment of the Invention, a very important advantage is the use of intercalating agents with different excitation optima. When the sample is energized at a wavelength which excites only the energy donor intercalator, but not the intercalator which serves to capture the hybrid, background emission is reduced, subsequently resulting in a more accurate quantitative determination of the target polynucleotides.

The TRF assay of the invention is more rapid and easier to perform than the complicated and lengthy assays so far available, in which overnight hybridization is often required, followed by antibody equilibration and washing steps before detection (see, e.g., Syvanen et al., supra).

DETAILED DESCRIPTION OF THE INVENTION

The following terms as used in the specification and claims hereof have the following meanings.

The term "sample" refers to those materials on which tests are performed, and includes biological, physiological, industrial, environmental and other types of solids and liquids. Of particular interest are biological tissues such as organ or musculoskeletal specimens or biopsies, cervical and peritoneal specimens or lavages and the like and fluids such as serum, plasma, urine, cerebrospinal fluid, saliva, milk, broth, and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluids which are tested by conventional methods are also encompassed by this term and can be assayed in accordance with the invention.

The terms "oligo- or polynucleotide target" or "target" refer to any nucleic acid-containing substance whose presence or absence is to be qualitatively or quantitatively determined in a sample. The assay of the present invention can be applied to the detection of target oligo- or polynucleotides which are at least partially present in single-stranded form or can be made at least partially single-stranded. The analyte, in functional terms, is usually selected from a naturally occurring or synthetic RNA or DNA for which a complementary nucleic acid exists or can be prepared.

The terms "oligo- or polynucleotide probe" or "probe" refer to any nucleic acid-containing compound or composite capable of recognizing a particular nucleic acid sequence in preference to other substances. In the majority of embodiments, the probes will be DNA hybridization assay oligonucleotide probes, such as those specific for disease-causing organisms, e.g., N. gonorrhoeae or human papilloma virus, or for identification of genetic disorders, e.g., Tay-Sach's disease or Down's syndrome.

The terms "linkage group", "linker arm", "linker" and the like refer to any of the well known bonds or compounds useful in joining functional groups and which do not substantially interfere with the characteristic properties or functions of the functional groups so joined. Examples of linkage groups which are useful in the present invention Include those described in Ward, et al., U.S. Pat. No. 4,711,955; Stavrianopoulos, U.S. Pat. No. 4,707,352 and Stavrianopoulos, U.S. Pat. No. 4,707,440.

The terms "intercalating moiety" or "intercalator" refer to those compounds capable of non-covalent insertion between the base pairs of a nucleic acid duplex and are specific in this regard only to double-stranded (ds) portions of nucleic acid structures including those portions of single-stranded nucleic acids which have formed base pairs, such as in "hairpin loops". The nucleic acid structures can be dsDNA, dsRNA or DNA-RNA hybrids.

It is well known that certain fluorescence-emitting dyes have the ability to become inserted noncovalently or intercalated between bases in the double-stranded helix. For example, 9-aminoacridine, a planar, heterocyclic molecule, is one such compound. Ethidium bromide, a phenanthridine dye, is another such intercalating agent. Publications describing the use of intercalating dyes in studies using nucleic acids include Georghiou, Photochemistry and Photobiology, 26:59–68, Pergamon Press (1977); Kubota, et al., Biophys. Chem., 6:279–284 (1977); Genest, et al., Nuc. Ac. Res., 13:2603–2615 (1985); Asseline, EMBO J., 3: 795–800 (1984); Richardson, et. al., U.S. Pat. No. 4,257, 774; and Letsinger, et. al., U.S. Pat. No. 4,547,569.

A phenanthridine dye, 6-(-4'-carboxyphenyl)-3,8-diamino-5-methyl phenanthridinium chloride from May and Baker Ltd., London, England (M-B 3492), has been shown to bind to and unwind closed circular double-stranded DNAs almost identically as the prototypical intercalcator, ethidium. See, Wakelin and Waring, Mol. Pharm., 9:544–561 (1974). A temperature lump study of the M-B 3492-DNA system confirmed that binding occurs by intercalation. See, Wakelin and Waring, J.Mol. Biol., 144:183–214 (1980).

The time resolved fluorescence (TRF) hybridization assay of the present invention is based in part on the above-described property of intercalation of specific compounds between the bases of the double-stranded nucleic acid helix. The principal feature of this invention is the use of two different intercalators, one of which serves to capture or fix the double-stranded hybrid which is formed between the target polynucleotide and the labeled polynucleotide probe, to a solid surface and a different intercalator, which can act as, an energy donor, or as an energy acceptor, or has attached thereto, a fluorescent compound which serves as either the energy donor/or the energy acceptor. The polynucleotide probe is labeled with either chelated lanthanide metals or fluorescent compounds, which serve as either energy donors or energy acceptors. The compounds chosen to serve as energy donors and energy acceptors must be such that transfer of energy can occur efficiently from a compound emitting energy at a first wavelength to a compound which absorbs energy at or near that wavelength and emits time-delayed or time-prolonged detectable energy at a second wavelength. For a further discussion of suitable energy transfer pair combinations, see the European Publication No. 0242527, supra, which publication as referred to above is based upon the priority document, U.S. application Ser. No. 831,250, filed on Feb. 19, 1986, which issued as U.S. Pat. No. 4,868,103 on Sep. 19, 1989. The disclosure of U.S. Pat. No. 4,868,103 is herein incorporated by reference, The disclosure of which is herein incorporated by reference.

As stated above, the use of the intercalator-substituted solid matrix is solely for the purpose of capturing and concentrating nucleic acids in double-stranded form. The solid matrix is not used for attaching either the target or the analyte, which is often the case in conventional assays, and where hybridization then proceeds in two phases. In the method of the invention, hybridization takes place between the target and the probe in solution, in which it occurs much more rapidly, as compared to the situation where one of the reactants is bound to a solid surface.

In the case where the intercalators serve both in the capture and in the energy transfer functions, the characteristic fluorescence emission of the intercalators used must be of different wavelengths, so that upon irradiation of the sample, energy transfer will occur only from the second intercalator. This avoids, or reduces, or eliminates background emission or quenching which would otherwise occur if the wavelength of excitation chosen were to be identical to that of the capture intercalator.

One preferred embodiment of the time-resolved fluorescence (TRF) assay is as follows. The sample containing the analyte of interest is solubilized and its DNA denatured. An aliquot thereof is then dispensed into a well, such as in a microscope slide, and covered with a cover slip, the surface of which has been derivatized with an intercalating agent. The derivatization typically involves first adding reactive amino groups to an acid-washed glass surface. The surface is then reacted with an intercalator which is derivatized with a linkage group that terminates in a substituent capable of reacting with amino groups. A preferred linkage group consists of six or more atoms.

The well also contains an excess of the analyte-specific moiety, which comprises a polynucleotide probe labeled with a lanthanide metal, and reagents necessary for efficient hybridization and stable chelation of the lanthanide metal to the probe.

Hybridization is allowed to proceed for 10–60 minutes, under conditions of salt, denaturation and temperature, such that hairpin structures in analytes or probes are prevented from being formed. See e.g., W. Saenger (1984) "Principles of Nucleic Acid Structure", pp. 116–58, Springer-Verlag, New York.

Chapter 6

Forces Stabilizing Associations Between Bases: Hydrogen Bonding and Base Stacking Before describing structural features of nucleotides and their oligo- and polymeric complexes, a few remarks about base–base interactions are in order. These interactions are of two kinds: (a) those in the plane of the bases (horizontal) due to hydrogen bonding and (b) those perpendicular to the base planes (base stacking) stabilized mainly by London dispersion forces and hydrophobic effects. Hydrogen bonding is most pronounced in nonpolar solvents where base stacking is negligible, and base stacking dominates in water where base–base hydrogen bonding is greatly suppressed due to competition of binding sites by water molecules. Both are individually accessible to measurement and have been investigated in detail, especially hydrogen bonding because it is fundamental to the genetic code. For reviews see Refs. (448,449).

6.1 Characterization of Hydrogen Bonds

Hydrogen bonds are mainly electrostatic in character. They play a key role in the stabilization of protein and nucleic acid secondary structure and have been the topic of several monographs and review articles (192,198,450–452,455,456). Therefore, in this discussion only some characteristics relevant to base–base hydrogen bonding will be described.

In general, a hydrogen bond

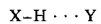

is formed if a hydrogen atom H connects two atoms X,Y of higher electronegativity. As hydrogen bonds are largely electrostatic in nature, their strength (reflected in the length of the H ··· Y distance) depends on (partial) charges located on X,H,Y. Hydrogen bonds with X = carbon and Y = oxygen have already been alluded to in Section 4.9, for charge densities see Figure 5-1.

Hydrogen-bonding interactions between bases are of the type N–

Elazar Rabbani et al.
Serial No. 08/486,053
Filed: June 7, 1995
Page 2 [Exhibit A to Supplemental Amendment to Applicants' January 28, 1999
    Amendment Under 37 C.F.R. §1.115 - April 8, 1999]

Table 6-1. Comparison of Some Energy Values in Covalent and Hydrogen Bonds

| Bond type | Bond length Å | Bond energy kcal/mole | Energy required for lengthening by 0.1 Å kcal/mole |
|---|---|---|---|
| Covalent | | | |
| C–C | 1.54 ± 0.02 | 83.1 | 3.25 |
| C–H (in ethane) | 1.09 ± 0.02[a] | 98.8[b] | 3.60[c] |
| Hydrogen bond | | | |
| O–H · · · O | 2.75 ± 0.2[d] | 3 to 6[c] | 0.1[b] |
| | (O · · · O distance) | | |

[a] From (197).
[b] From (198).
[c] From (455).
[d] From (456).

H · · · N and N–H · · · O with the donor N–H group of either the amino or imino type. In some modified bases containing thioketo groups, N–H · · · S hydrogen bonds also occur, although in general sulfur is thought to be a weaker hydrogen bond acceptor than oxygen (453,454).

Hydrogen bonds are "soft" and only weakly directional. Compared with covalent bonds with well-defined length, strength, and orientation, hydrogen bonds are about 20 to 30 times weaker (Table 6-1). Therefore they are more susceptible to bending and stretching, and this results in variable geometries for the X–H · · · Y system (Table 6-2). In some extreme cases with long H · · · Y distances, the usual criterion that H · · · Y should be shorter than the sum of the van der Waals radii might not be sufficient. In these instances, Allinger's van der Waals' potential minimum contact radii (Table 3-1) can instead be used to relax the criterion considerably (158, 451). Relatively "long," weak hydrogen bonds have been observed when two acceptors $Y_1$, $Y_2$ compete for the same hydrogen atom in bifurcated or "three-centered" systems (321,451):

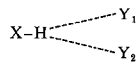

Additivity and cooperativity of hydrogen bonds. Under the influence of a hydrogen bond, the charges on the atoms involved are modified due to polarization, H becoming more electropositive and X,Y more negative. This effect leads to increased affinity of X,Y for accepting further hydrogen bonds. If Y is the oxygen atom of a hydroxyl group, the hydrogen attached to it will also be affected by polarization and becomes a better donor. Since this cooperativity (451) holds in general for bifunctional X–H · · · X–H · · · X–H · · · systems where each donor plays simultaneously the role of an acceptor and vice versa, it can involve nucleoside Enz-39(C2)

Elazar Rabbani et al.
Serial No. 08/486,053
Filed: June 7, 1995
Page 3 [Exhibit A to Supplemental Amendment to Applicants' January 28, 1999
 Amendment Under 37 C.F.R. §1.115 - April 8, 1999]

Table 6-2. Some Geometrical Characteristics of Hydrogen Bonds Involved in Base-Base Interactions [From (192, 321, 450, 453, 454)]

| System | Distances or angles | | Mean |
|---|---|---|---|
| | Minimum | Maximum | |
| N–H · · · N | | | |
| N · · · N | 2.75 | 3.15 | 2.90 |
| N–H | 0.86 | 1.02 | 0.95 |
| H · · · N | 1.78 | 2.02 | 1.99 |
| N⟨H⟩N | 2° | 17° | 9° |
| N–H · · · O | | | |
| N · · · O | 2.74 | 3.07 | 2.95 |
| N–H | 0.83 | 1.06 | 0.95 |
| H · · · O | 1.83 | 2.17 | 1.95 |
| N⟨H⟩O | 3° | 23° | 9° |
| O–H · · · O | | | |
| O · · · O | 2.60 | 3.05 | 2.73 |
| O–H | 0.68 | 1.16 | 0.86 |
| H · · · O | 1.74 | 2.20 | 1.95 |
| O⟨H⟩O | 1° | 20° | 8° |
| N–N · · · S | | | |
| N · · · S | 3.25 | 3.55 | 3.32 |
| N–H | 0.84 | 1.04 | 0.95 |
| H · · · S | 2.27 | 2.57 | 2.40 |
| N⟨H⟩S | 1° | 25° | 15° | hydroxyls as well as bases, because these display a formally analogous electronic structure:

Here, Z represents (unsubstituted) ring nitrogen or keto oxygen. The equivalence to a simple X–H system becomes clear if electrons are delocalized:

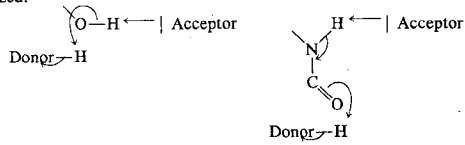

Elazar Rabbani et al.
Serial No. 08/486,053
Filed: June 7, 1995
Page 4 [Exhibit A to Supplemental Amendment to Applicants' January 28, 1999
  Amendment Under 37 C.F.R. §1.115 - April 8, 1999]

Besides geometrical factors involved, this scheme suggests that bases form preferentially complexes with at least two (cyclic) hydrogen bonds. We should even expect that under the influence of the cooperative effect, hydrogens in base-pairs can jump in concerted mechanism from the donor in one base to the acceptor on the partner base:

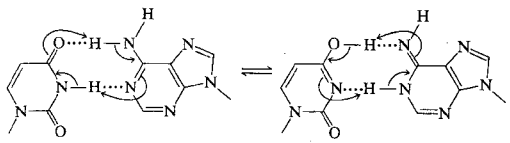

The hydrogen transfer would be only of minor importance on base-pair geometry and, above all, it would not disturb Watson-Crick type recognition because complementarity within the base-pair is obeyed at all times. A recent NMR study on tRNA in aqueous solution has in fact estimated that 5 to 15% of all base-pairs are in such imino/enol form at a given time, with rate constants as slow as 100 to 300 per second (456a). However, the spectra can also be explained in other ways (anisotropy effects) and it appears more likely that hydrogen atoms remain in their amino/keto positions and do not jump.

6.2 Patterns of Base–Base Hydrogen Bonding: The Symmetry of a Polynucleotide Complex Interactions between like (homo) and different (hetero) bases have been observed in crystal structure analyses of individual bases, nucleosides, or nucleotides and of complexes formed by two or more different compounds of this type [reviewed in (192)]. Under the assumption that at least two "cyclic" $N-H \cdots O$ or $N-H \cdots N$ hydrogen bonds must form in order to produce a stable base-pair, the four bases substituted at the glycosyl nitrogens ($N_1$ in pyrimidine and $N_9$ in purine) can be arranged in 28 different ways (Figure 6-1) (33,457).

Twenty-eight base-pairs with dyad, pseudodyad, and no symmetry. The 28 base-pairs are grouped in Figure 6-1 according to interactions between like and different bases in the purine–purine and pyrimidine–pyrimidine series, followed by purine–pyrimidine pairs. In each group, the orientations of glycosyl $C_{1'}-N$ linkages can be either unrelated by symmetry elements (asymmetric) or related by dyads (twofold axes) located perpendicular to or within the base-pair planes as indicated by symbols ● and ↑ (Figure 6-2). Note that the dyads in the homopurine and homopyrimidine base-pairs, I to IV and XII to XV, transform one base exactly into the Elazar Rabbani et al.
Serial No. 08/486,053
Filed: June 7, 1995
Page 5 [Exhibit A to Supplemental Amendment to Applicants' January 28, 1999
    Amendment Under 37 C.F.R. §1.115 - April 8, 1999]
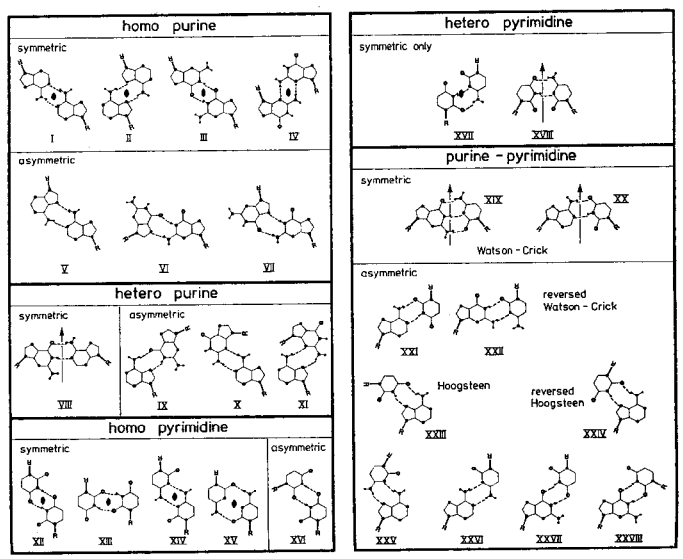
Enz-39(C2)

Elazar Rabbani et al.
Serial No. 08/486,053
Filed: June 7, 1995
Page 6 [Exhibit A to Supplemental Amendment to Applicants' January 28, 1999
    Amendment Under 37 C.F.R. §1.115 - April 8, 1999]

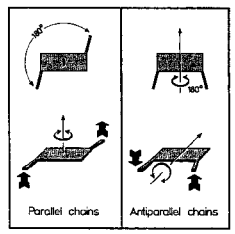

Figure 6-2. Base-pairs can display two kinds of twofold symmetry, depending on the orientations of the glycosyl $C_{1'}$–N bonds. In this illustration, the latter are indicated as sticks protruding from rectangular plates representing base-pair planes. Twofold rotation axes (dyads) can be arranged either perpendicular to (left) or within the base-pair planes (right); this determines the orientation of the attached sugar–phosphate groups or backbones. In a double helix, the two strands are parallel to each other if the dyad is perpendicular to the base-pair (and therefore coinciding with the helix axis; left) and they are running in opposite direction, antiparallel, if dyads are within the base-pair plane and consequently perpendicular to the axis of the double helix (right). The Watson–Crick type DNA or RNA corresponds to this latter arrangement; see also Figures 6-3(a) and (b).

other. However, in heteropurine and heteropyrimidine (VIII and XVII, XVIII) and in the purine–pyrimidine Watson–Crick base-pairs (XIX and XX), the operation of the dyad is restricted to the glycosyl $C_{1'}$–N linkage and not applicable to the bases. It is therefore called pseudo-dyad.

Symmetry elements are also found in polynucleotide complexes. The symmetry elements are of special interest because in polynucleotide complexes (Chapters 9–13) they relate not only the glycosyl bonds but also the attached sugar–phosphate backbones. As a consequence, base-pairs with dyads *perpendicular* to the base planes (symbol ●) direct the 3'→5' orientations of the backbones parallel and identical to each other, whereas a dyad *within* a base-pair (symbol ↑) gives rise to antiparallel

---

Figure 6-1. The 28 possible base-pairs for A, G, U(T), and C involving at least two (cyclic) hydrogen bonds. Hydrogen and nitrogen atoms displayed as small and large filled circles, oxygen atoms as open circles, glycosyl bonds as thick lines with R indicating ribose $C_{1'}$ atom. Base-pairs are boxed according to composition and symmetry, consisting of only purine, only pyrimidine, or mixed purine/pyrimidine pairs and asymmetric or symmetric base-pairs. Symmetry elements ● and ↑ are twofold rotation axes vertical to and within the plane of the paper (see Figure 6-2). In the Watson–Crick base-pairs XIX and XX and in base-pairs VIII and XVIII, pseudosymmetry relating only glycosyl links but not individual base atoms is observed. Drawn after compilations in (33,457).

Elazar Rabbani et al.
Serial No. 08/486,053
Filed: June 7, 1995
Page 7 [Exhibit A to Supplemental Amendment to Applicants' January 28, 1999
Amendment Under 37 C.F.R. §1.115 - April 8, 1999]

orientations of identical backbone structures; see hands in Figure 6-2. An example of the parallel case is poly (AH$^+$)]$_2$ with base-pair II of Figure 6-1 (458) and examples of antiparallel structures are DNA, RNA, and poly (A) · poly(U) all of which display Watson–Crick-type base-pairs (8). A special case is encountered with poly(U) and the 2-thioketo derivative poly(s$^2$U) both of which form antiparallel double helices with the asymmetric base-pair XVI. As a result, the two sugar–phosphate backbones are not identical to each other but have different conformations (459–461) (Chapter 13).

The term "symmetry related" applies in a strict sense only to crystalline polynucleotide complexes. In these, the space group dyads coincide with dyads relating glycosyl links (Figure 6-2). Therefore, space group constraints must be obeyed and the molecule is subject to crystallographic law and order. However, if the material is dissolved and escapes the limiting lattice, the overall, gross symmetry properties will be largely retained but they break down in crystallographic terms. A good example is presented by crystalline fibrous DNA which in the B form is pierced by a space group dyad and repeats exactly after 10 base-pairs (= one turn or one $c$-axial length). In solution and when DNA is adsorbed on a flat surface, however, repeat lengths of 10.4 ± 0.1 and 10.6 ± 0.1 base-pairs are observed (462,463). Moreover in a crystalline, double-helical DNA dodecanucleotide no space group dyad is colinear with a base-pair dyad; the overall repeat is 10.3 to 10.4 base-pairs (464), and for the central 6 base-pairs repeat lengths of about 9.8 nucleotides are observed (Chapter 10).

6.3 Detailed Geometries of Watson–Crick and Hoogsteen Base-Pairs

It is worthwhile to look at the Watson–Crick and Hoogsteen base-pairs more closely (Figures 6-3 and 6-4). The data entered in Figure 6-3(a) were obtained from the X-ray crystal structure analyses of ApU (465) and GpC (466) which located all second row atoms of the base-pairs but not hydrogens; the hydrogen atoms are shown in positions calculated from the C, Figure 6-3. (a) Watson–Crick base-pairs observed in crystal structures of GpC (top) and ApU (bottom). Hydrogen atoms were not located experimentally but are calculated from the positions of the other atoms. Note differences in hydrogen bond lengths N–H · · · O, from 2.86 to 2.95 Å, and N–H · · · N, from 2.82 to 2.95 Å, consistent with the spread given in Table 6-1 and reflecting the "softness" of this type of interaction. The distances between glycosyl C$_{1'}$ atoms, 10.46 Å and 10.67 Å, are remarkably similar and are the basis, together with the almost co-inciding angles, C$_{1'}$· · ·C$_{1'}$–N, around 53°, of the observed geometrical isomorphism. From (465,466). (b) Schematic description of isomorphism and pseudo-symmetry in Watson-Crick base-pairs.

Enz-39(C2)

Elazar Rabbani et al.
Serial No. 08/486,053
Filed: June 7, 1995
Page 8 [Exhibit A to Supplemental Amendment to Applicants' January 28, 1999
Amendment Under 37 C.F.R. §1.115 - April 8, 1999]
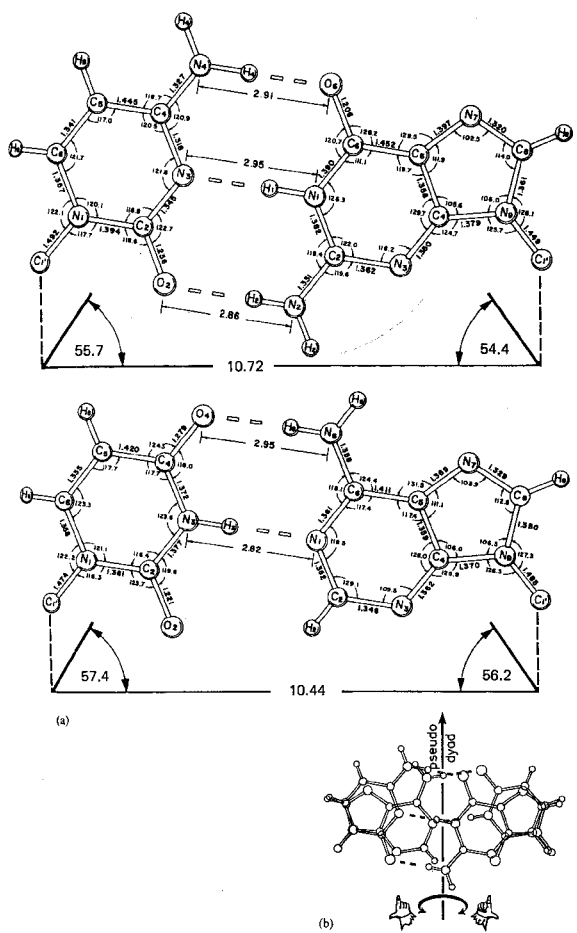
Enz-39(C2)

Elazar Rabbani et al.
Serial No. 08/486,053
Filed: June 7, 1995
Page 9 [Exhibit A to Supplemental Amendment to Applicants' January 28, 1999
    Amendment Under 37 C.F.R. §1.115 - April 8, 1999]
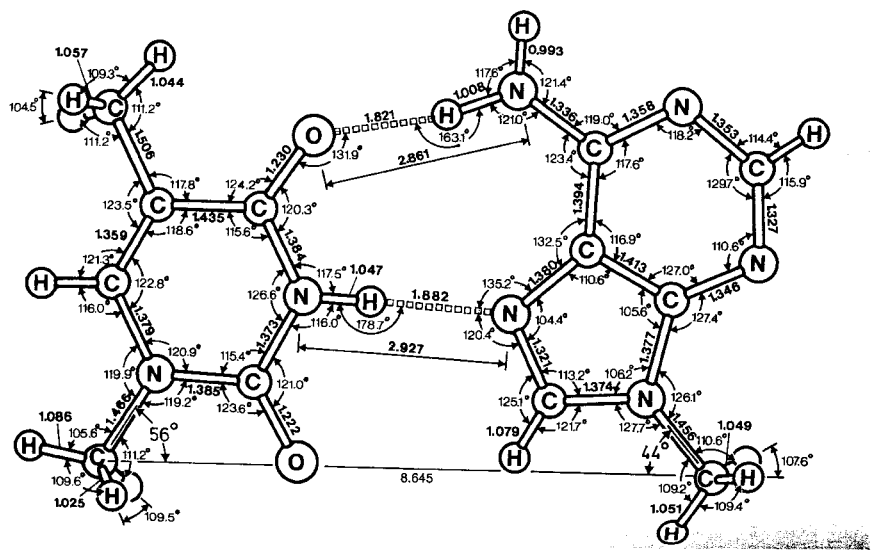
Enz-39(C2)

Elazar Rabbani et al.
Serial No. 08/486,053
Filed: June 7, 1995
Page 10 [Exhibit A to Supplemental Amendment to Applicants' January 28, 1999
    Amendment Under 37 C.F.R. §1.115 - April 8, 1999]

N, and O atoms. In Figure 6-4 the 9-ethyladenine:1-methylthymine Hoogsteen pair as derived from an accurate neutron diffraction study is displayed, with all hydrogen positions experimentally determined.

Geometrical isomorphism and propeller twist. In the A–U and G–C Watson–Crick base-pairs, the structural isomorphism is noteworthy; i.e., the overall shapes and dimensions are comparable. The $C_{1'} \cdots C_{1'}$ distances are ~0.3 Å smaller for A:U than for G:C and the angles which these lines form with the glycosyl $C_{1'}$–N bonds are between 54.4° and 57.4°. Neglecting the small difference of 3°, we can say that the glycosyl links are related by a pseudodyad (Figure 6-3(b)).

The two bases in the A:U and G:C pairs are not coplanar. They are twisted about the hydrogen bonds like the blades of a propeller. This twist is about 12° in A:U and 7° in G:C. Comparable twists have also been observed in other base-pairs (192).

In contrast, the bases in the Hoogsteen pair (Figure 6-4) (467) are perfectly coplanar because they are located on a crystallographic mirror plane. In other crystal structures of Hoogsteen A:U base-pairs, however, where such crystallographical constraint is absent, a propeller-like twist similar to the Watson–Crick base-pairs has been observed, with 9° in 9-ethyladenine:1-methyl-5-iodouracil (468). Compared with the Watson–Crick base-pair, in the Hoogsteen pair the $C_{1'} \cdots C_{1'}$ distance, 8.645 Å, is reduced by about 2 Å and the angles between this line and the glycosyl $C_{1'}$–N bonds differ by more than 10° between purine and pyrimidine bases; i.e., a pseudodyad is not present.

A structural disorder: Hoogsteen and reversed Hoogsteen base-pairs. As discovered in the neutron study (467) and mentioned by Hoogsteen in his original paper (469), there is some disorder in the 1-methylthymine:9-methyladenine crystal structure, with 10–13% of the 1-methylthymine molecules rotated 180° about the $C_6$–$N_3$ axis. This simultaneous occurrence of Hoogsteen and reversed Hoogsteen base-pairs (XXIII and XXIV in Figure 6-1) can be explained by the symmetrical shape of 1-methylthymine. The rotation leads to substitution of $O_4$ by $O_2$, maintaining the hydrogen-bonding scheme. A reversal of this behavior is found in the complex 1-methyl-5-bromouracil:9-ethyladenine (with the 5-bromo group substituting for the 5-methyl in thymine) where only 6% of the 1-methyl-5-bromouracil molecules are in the Hoogsteen base-pairing scheme and 94% are in the reversed Hoogsteen mode (470). It could be argued that the altered electronic structure in 5-bromouracil relative to thymine determines the configuration of these base-pairs. However, the crystal struc-

---

Figure 6-4. Hoogsteen base-pair formed by 9-ethyladenine:1-methylthymine. Data obtained from a neutron study which experimentally located hydrogen atoms (467). Note differences in $C_{1'} \cdots C_{1'}$–N angles, 56° and 44°, and the relatively short $C_{1'} \cdots C_{1'}$ separation of 8.465 Å. NH $\cdots$ O and NH $\cdots$ N hydrogen bonds are indicated by broken lines.

Enz-39(C2)

Elazar Rabbani et al.
Serial No. 08/486,053
Filed: June 7, 1995
Page 11 [Exhibit A to Supplemental Amendment to Applicants' January 28, 1999
Amendment Under 37 C.F.R. §1.115 - April 8, 1999]

ture of 1-methyl-5-fluorouracil:9-ethyladenine which features a Hoogsteen base-pair suggests that crystal packing and base stacking effects may be the dominant factors (471).

6.4 The Stability and Formation of Base Pairs as Determined by Thermodynamic, Kinetic, and Quantum Chemical Methods: Electronic Complementarity

Base–base interaction through hydrogen bonding has been investigated by thermodynamic methods in order to derive association constants as well as enthalpies and entropies for this process. Complex formation in water is relatively weak due to competition of water molecules for hydrogen bond donor and acceptor sites, and therefore, only qualitative data can be obtained. For the 5'-nucleotides, NMR downfield shifts of amino group signals gave the following sequence of decreasing association (base-pair formation) tendencies (204):

GMP with CMP > UMP > IMP >> AMP,
AMP with UMP ~ CMP >> IMP, GMP,
CMP with GMP ~ CMP > UMP > XMP, AMP, IMP.

For more quantitative data, apolar solvents must be used where hydrogen bonding is pronounced and where stacking interactions between bases are negligible (204). Several studies were carried out using bases substituted at the glycosyl nitrogen and solvents such as tetrachloromethane, chloroform, and dimethylsulfoxide. Base–base association has been monitored as change in amino group signals by both NMR and IR methods (Figure 6-5) (472,473), and has been studied by calorimetric and osmometric methods.

In solution, a mixture of Watson–Crick and Hoogsteen base-pairs are formed with at least two hydrogen bonds and involving all potential binding sites. The data summarized in Figure 6-6 show that the association constants depend greatly on the chemical nature of the two partners. In the 9-ethyladenine:1-cyclohexyluracil series, the 3-methyluracil derivative does not form a complex with adenine. This indicates that, for dimer association, one hydrogen bond between the adenine amino group and uracil carbonyl oxygens is not sufficient; at least two hydrogen bonds (a cyclic dimer) are required. It is obvious that the association constants depend on the acidity of the uracil imino hydrogen (Figure 5-3), low acidity as in 5,6-dihydro-1-cyclohexyluracil ($pK = 11$) correlating with weak association, and high acidity as in the 5-bromo- derivative ($pK = 7.8$) with strong association. In the 4-thiouracil compound ($pK = 7.4$), the acidity effect is counterbalanced by the weak hydrogen bond acceptor properties of the sulfur atom.

Elazar Rabbani et al.
Serial No. 08/486,053
Filed: June 7, 1995
Page 12 [Exhibit A to Supplemental Amendment to Applicants' January 28, 1999 Amendment Under 37 C.F.R. §1.115 - April 8, 1999]

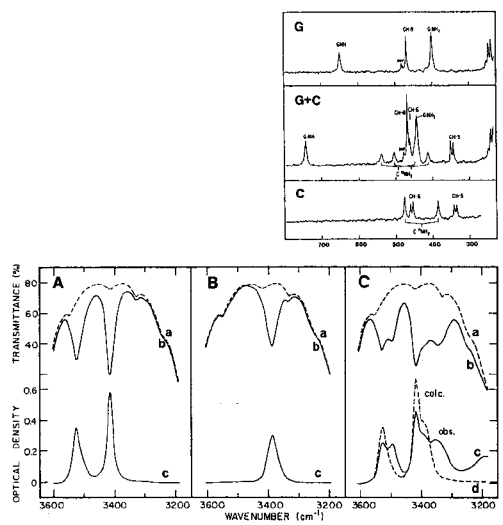

Figure 6-5. Monitoring base–base associations. (Top) Proton NMR spectra of 9-methylguanine (G), 1-[7-$^{15}$N]methylcytosine (C), and their 1:1 mixture (G + C) in deuterated dimethylsulfoxide/dimethylformamide. $^{15}$N-Substituted cytosine was used in order to display the C–$^{15}$NH$_2$ doublet which otherwise would be obscured by signals from aromatic protons. Recorded with a Varian A-60 spectrometer; abscissa given in cps (cycles per second) as downfield shifts from internal TMS (tetramethylsilane) standard. From (472). (Bottom) Infrared absorption spectra of 2,6-diamino-9-ethylpurine (A), 1-cyclohexyl-5-bromouracil (B), and their 1:1 mixture (C), all at 0.002 $M$ in deuterochloroform. In the upper part of this picture, absorption spectra of pure solvent (a) and of solutions (b) are recorded. In the lower part difference spectra (a − b) are plotted as optical density (c). Dashed curve (d) gives calculated sum of the optical density curves in A(c) and B(c); difference with measured curve C(c) directly indicates presence of hydrogen-bonded complexes. From (473).

In the series with 9-ethyladenine derivatives (Figure 6-6), compare the association constants for complex formation of 1-cyclohexyluracil with those for 9-ethyl-6-methylaminopurine, 9-ethyl-2-aminopurine, and 9-ethyladenine. The latter (100 liters/mole) is twice that of the former two (50 and 45 liters/mole), suggesting that adenine binds uracil derivatives in Enz-39(C2)

Elazar Rabbani et al.
Serial No. 08/486,053
Filed: June 7, 1995
Page 13 [Exhibit A to Supplemental Amendment to Applicants' January 28, 1999
Amendment Under 37 C.F.R. §1.115 - April 8, 1999]

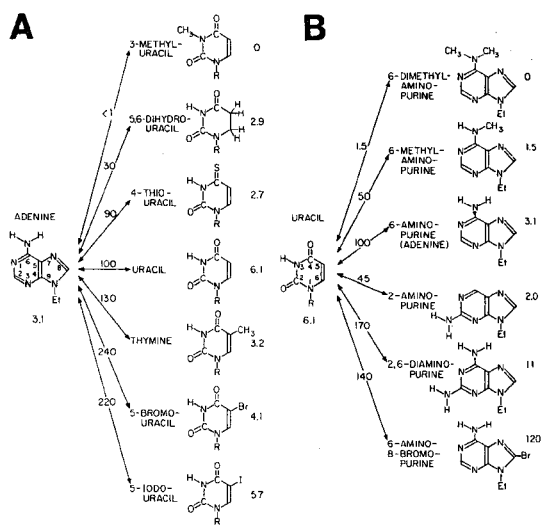

Figure 6-6. Association constants (liters/mole) for base-pair formation between various substituted 1-cyclohexyluracil and 9-ethyladenine derivatives, measured in deuterochloroform solution at 25°C using infrared methods displayed in Figure 6-5. Numbers near arrows are constants for association between adenine and uracil derivatives whereas figures shown close to structural formulas are self-association constants. (A) Association of 9-ethyladenine with uracil derivatives. (B) Association of 1-cyclohexyluracil with adenine derivatives. From (473).

Watson–Crick and Hoogsteen mode (base-pairs XX and XXIII in Figure 6-1) and thus has a statistical advantage of two binding sites with respect to the other two compounds. In all cases, Watson–Crick and reversed Watson–Crick, Hoogsteen and reversed Hoogsteen base-pairs cannot be differentiated so that all data for A : U association refer to a combination of base-pairs.

Hydrogen bonding to $O_2/O_4$ in uracil is determined by electronegativity. The mixture of A : U base-pairs has been studied by $^{13}C$ NMR methods looking at signals assigned to $C_2$- and $C_4$-carbonyl carbons in 1-cyclohexyluracil derivatives when complexed with 9-ethyladenine in chloroform, i.e., in a system identical to that above (Figure 6-6). For A : U asso- Enz-39(C2)

Elazar Rabbani et al.
Serial No. 08/486,053
Filed: June 7, 1995
Page 14 [Exhibit A to Supplemental Amendment to Applicants' January 28, 1999
Amendment Under 37 C.F.R. §1.115 - April 8, 1999]

ciation, the frequency of $O_4$ binding decreases and that of $O_2$ binding increases in the order (474)

thymine > uracil > 5-bromouracil > 4-thiouracil.

This sequence parallels the electronegativity of the $O_4$ oxygen in these compounds; the 5-methyl group in thymine pushes electrons and provides more electronegativity at $O_4$ whereas the 5-bromo group withdraws electrons and has an opposite effect. This latter observation could explain why incorporation of 5-bromouridine into DNA leads to mutations via mispairing. If $O_2$ is more likely to be involved in hydrogen bonding than $O_4$ (in contrast to thymidine), then it is quite obvious that G:5-BrU pairing (base-pair XXVIII in Figure 6-1) can form without involving improbable tautomeric forms of 5-bromouracil to simulate a G:C geometry (475).

At high concentrations, oligomeric base multiplets can form. Under usual experimental conditions, A:U complexes are dimers and not trimers or higher oligomers and the same holds for the self-association, U:U and A:A. This is clear from an IR band observed at 3490 cm$^{-1}$ which is attributed to a free amino N–H hydrogen in adenine and which should disappear if both Watson–Crick and Hoogsteen binding sites are simultaneously occupied (Figure 6-7). Such higher complexes do indeed occur at elevated concentrations (476) and they are of importance in trimer formation of one poly(A) with two poly(U) chains, poly(A) · 2poly(U); see Chapter 10.

Thermodynamic data describing formation of homo- and heterocomplexes of the four bases are summarized in Table 6-3 (476–480). It is evident that solvent effects have a strong influence on binding constants and enthalpies, and that in general the self-associates are less stable than the complementary A:U and G:C base-pairs. The loss in entropy (−11 to −16 e.u.), however, is comparable in all cases, and this suggests that the overall structures of the associates are similar, dimeric complexes stabilized by at least two (cyclic) hydrogen bonds. If the enthalpy of base-pair-

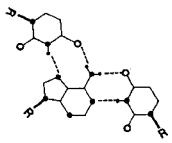

Figure 6-7. In the base trimer A:2U, both Watson–Crick and Hoogsteen base-pairing sites of A are engaged simultaneously. ●, nitrogen; O, oxygen; the glycosyl link is indicated by the solid line. In this illustration, only normal Watson–Crick and Hoogsteen pairs are drawn as formed in the poly(A):2 poly(U) triple helix, (Section 10.2). If these as well as reversed base-pairs are utilized four different schemes emerge.

Enz-39(C2)

Elazar Rabbani et al.
Serial No. 08/486,053
Filed: June 7, 1995
Page 15 [Exhibit A to Supplemental Amendment to Applicants' January 28, 1999
Amendment Under 37 C.F.R. §1.115 - April 8, 1999]

Table 6-3. Thermodynamic Data for Complementary and Self-pairing of Bases via Hydrogen Bonding

| Compounds, solvents, and methods | Reaction | $K_{assoc.}$ [l/mole] | $-\Delta H$ [kcal/mole] | $-\Delta S$ [e.u.] |
|---|---|---|---|---|
| Guanosine, Cytidine in dimethylsulfoxide NMR, 32°C[a] | $G+G \rightleftharpoons G_2$ | 0.18 | 1.0 ± 1 | |
| | $C+C \rightleftharpoons C_2$ | 0.1 | 1.7 ± 1.5 | |
| | $G+C \rightleftharpoons GC$ | 3.7 ± 0.6 | 5.8 | 16 |
| 9-Ethyladenine, 1-Cyclohexyluracil in chloroform IR, 25°C[b] | $A+A \rightleftharpoons A_2$ | 3.1 ± 0.3 | 4.0 ± 0.8 | 11.4 ± 2 |
| | $U+U \rightleftharpoons U_2$ | 6.1 ± 0.6 | 4.3 ± 0.4 | 11.0 ± 1 |
| | $A+U \rightleftharpoons AU$ | 103 ± 36 | 6.2 ± 0.6 | 11.8 ± 1.2 |
| 1-Methylpyrimidine, 9-Methylpurine in vacuum mass spectrum[c] | $A+U \rightleftharpoons AU$ | | 14.5 | |
| | $G+C \rightleftharpoons GC$ | | 21.0 | |
| | $U+U \rightleftharpoons U_2$ | | 9.5 | |
| | $C+C \rightleftharpoons C_2$ | | 16.0 | |

[a] From (477).
[b] From (478).
[c] From (480).

ing, around 6 kcal/mole dimer, can be attributed to only hydrogen-bonding effects, then 2 to 3 kcal/mole is released per mole hydrogen bond formed, a value within the normally accepted range for such interactions (Table 6-1). The "vacuum" data, however, obtained for the gaseous state indicate enthalpies of around 7 kcal/mole per hydrogen bond (480).

Rates of base–base association are diffusion controlled. Using ultrasonic attenuation measurements, the kinetics of base–base association have been determined for the system 9-ethyladenine:1-cyclohexyluracil in chloroform. Rates of duplex formation for both homo- and heterocomplexes are practically diffusion controlled and are similar in all three cases (481) (Table 6-4). The dissociation rates, however, are slower for A:U than for A:A and U:U, indicating that the relative strengths of the base-pair hydrogen bonds decrease A:U > A:A ~ U:U, as already suggested by the respective association constants.

Electronic complementarity is of major importance for specific base–

Table 6-4. Rate Constants for Association and Dissociation of 9-Ethyladenine and 1-Cyclohexyluracil in Chloroform [From (481)]

| | Rate constant | | | |
|---|---|---|---|---|
| Reaction | Association (mole$^{-1}$ · sec$^{-1}$) | Dissociation (sec$^{-1}$) | Temperature (°C) | |
| $U+U \rightleftharpoons U_2$ | $1.5 \times 10^9$ | $25 \times 10^7$ | 25 | |
| $A+A \rightleftharpoons A_2$ | $\geq 2 \times 10^9$ | $\geq 60 \times 10^7$ | 25 | |
| $A+U \rightleftharpoons AU$ | $4.0 \times 10^9$ | $3.2 \times 10^7$ | 20 | $\Delta H = -6.1$ kcal/mole |

Elazar Rabbani et al.
Serial No. 08/486,053
Filed: June 7, 1995
Page 16 [Exhibit A to Supplemental Amendment to Applicants' January 28, 1999
    Amendment Under 37 C.F.R. §1.115 - April 8, 1999]

base interactions. This has been demonstrated by quantum chemical studies (482–485) which are summarized for a few selected base-pair combinations in Table 6-5. The separation of the total hydrogen-bonding interaction energy $E_{tot}$ into contributions from dispersion ($E_d$), polarization ($E_p$), and electrostatic ($E_{el}$) effects clearly shows that the latter by far dominate and account for about 80% of the total energy; i.e., hydrogen bonds are mainly electrostatic in nature. From the variation of total energies ($E_{tot}$) with base-pair constitutents, it becomes clear that the stability of such a complex is not merely defined by the number of hydrogen bonds. Rather, it is necessary to consider the intrinsic electronic structures of associated bases, a fact previously deduced from measurements of binding constants and termed "*electronic complementarity*" (473).

The relative $E_{tot}$ values for different base-pairs suggest that complementary pairs in the Watson–Crick sense are more stable than the self-associates of the individual components. All noncomplementary base-pairs such as A:G and G:U are less stable than the corresponding self-associate pairs. This finding explains why noncomplementary pairs have not been crystallized except for substituted bases like 5-fluorouracil complexing with cytosine (486,487) which have an altered electronic structure and therefore exhibit binding energies different from those of the natural analogs. A special role is assigned to some "wobble" base-pairs discussed in Section 6.9.

Table 6-5. Interaction Energies ($E_{total}$) in Some Selected Base–Pairs Calculated by Quantum Chemical Methods [From (484)]

| Base–pair[a] | Energy contributions [kcal/mole] | | | |
|---|---|---|---|---|
| | E electrostatic | E polarization | E dispersion | E total |
| Complementary Watson-Crick and Hoogsteen Base–Pairs | | | | |
| G–C (XIX) | −14.10 | −1.90 | −0.79 | −16.79 |
| A–T (XX) | − 5.7 | −0.57 | −0.73 | − 7.00 |
| A–T (XXI) | − 5.47 | −0.64 | −0.86 | − 6.97 |
| A–U (XX) | − 5.68 | −0.66 | −0.87 | − 7.21 |
| A–U (XXIII) | − 4.93 | −0.70 | −0.98 | − 6.61 |
| A–U (XXIV) | − 5.26 | −0.64 | −0.95 | − 6.85 |
| Self-Complementary Base–Pairs | | | | |
| A–A (V) | − 4.40 | −0.49 | −0.71 | − 5.60 |
| U–U (XII) | − 4.13 | −0.61 | −0.68 | − 5.42 |
| G–G (III) | −13.71 | −1.72 | −0.61 | −16.04 |
| C–C (XIV) | − 8.61 | −1.41 | −0.71 | −10.73 |
| A–G (VIII) | − 7.68 | −1.02 | −0.70 | − 9.40 |
| G–U (XXVIII) | − 6.08 | −1.12 | −0.67 | − 7.78 |

[a] Roman numerals in parentheses refer to base–pairs in Figure 6-1.

Elazar Rabbani et al.
Serial No. 08/486,053
Filed: June 7, 1995
Page 17 [Exhibit A to Supplemental Amendment to Applicants' January 28, 1999
    Amendment Under 37 C.F.R. §1.115 - April 8, 1999]

6.5 Patterns of Vertical Base–Base Interactions

Bases pile up in long stacks like coins in a roll. Horizontal base–base association via hydrogen bonding is observed in nonaqueous solvents and in the gaseous and crystalline states. Additionally, in the solid state bases are found almost exclusively stacked such that one base plane is at the van der Waals distance, ~3.4 Å, and parallel to the adjacent one, an arrangement due to vertical rather than horizontal interactions. In aqueous solution, such base stacks form as well. Since stacking is important for the stabilization of nucleic acid helices (488,489), the principal geometric and thermodynamic features and the main forces responsible for the interactions will be discussed here. For a review, see (448).

In two comparative studies (490,491), packing patterns of bases, of charge–transfer complexes, and of nonpolar aromatics such as benzene, naphthalene, anthracene, and phenanthrene were described. The nonpolar aromatics have no dipole moments and crystallize in a herringbone-type arrangement with adjacent molecules perpendicular rather than parallel to each other. If, however, as in acridine and ethidium, a nitrogen is introduced into anthracene or phenanthrene to create a dipole moment, the molecules orient parallel to each other in the crystal lattice and form long stacks.

Recurring stacking patterns suggest specificity. Stacked arrangements are also dominant in crystal structures of bases (490,491). It is striking to find that the stacking patterns in these bases are rather specific, with polar substituents $-NH_2$, $=N-$, $=O$ or halogen of one base superimposed over the aromatic system of the adjacent base (Figure 6-8). This kind of stacking specificity even overrides hydrogen-bonding effects. In the series deoxyadenosine monohydrate (492), adenosine 5'-phosphate (493), adenosine:5-bromouridine (494), deoxyguanosine:5-bromodeoxyuridine (398), the purine bases all stack in the pattern described in Figure 6-8a although crystal space groups, cell dimensions, molecular packing, and hydrogen-bonding schemes differ from each other. Similarly, the stacking specificity is pronounced in halogenated bases. Halogen atoms are located over the adjacent heterocycle, with even less than a van der Waals distance between halogen atoms and atoms of the heterocycle (Figure 6-8i).

Several nucleoside and nucleotide crystal structures display close intermolecular contacts between sugar $O_{4'}$ atoms and adjacent heterocycles (Figures 6-8a,j). This kind of interaction is probably due to the relatively low electronegativity of $O_{4'}$ (Section 5.1.), which encourages close approach to a $\pi$-electronic system.

No stacking at all is found in some crystal structures of protonated pyrimidine bases and nucleotides, suggesting that charged pyrimidines tend to unstack. In the purine series, however, stacking is observed but Enz-39(C2)

Elazar Rabbani et al.
Serial No. 08/486,053
Filed: June 7, 1995
Page 18 [Exhibit A to Supplemental Amendment to Applicants' January 28, 1999
Amendment Under 37 C.F.R. §1.115 - April 8, 1999]

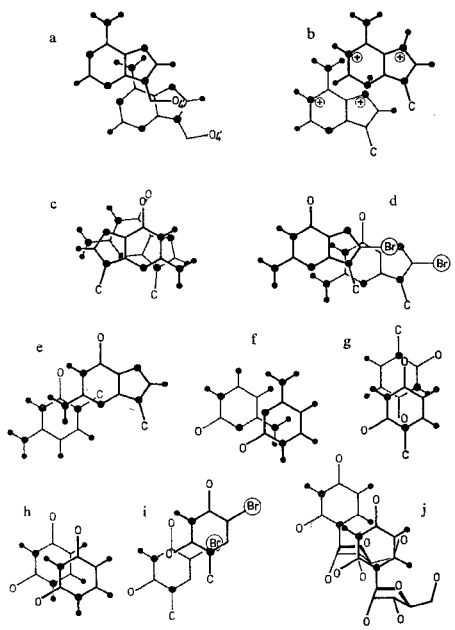

Figure 6-8. Stacking patterns of bases in different crystal structures (redrawn from 491). (a) The same adenine stack occurs in different crystal structures: deoxyadenosine monohydrate (492), adenosine 5'-phosphate (493) and adenosine:5-bromouridine complex (494); (b) stacking of protonated purines, 9-methyladenine dihydrobromide (415); (c) stacking pattern in guanosine and inosine crystal structures (495); (d) influence of halogen substituent on stacking pattern in 8-bromoguanosine (496), compare with (c); (e-g) interaction between amino or keto substituents and purine or pyrimidine bases: (e) 9-ethylguanine:1-methyl-5-fluorocytosine (497); (f) cytosine monohydrate (498); (g) 9-ethyladenine:1-methyluracil (499); (h) pyrimidine overlap involving ring nitrogen atom in uracil (500); (i) influence of halogen substituent on pyrimidine stacking in 5-bromouridine (501) and in 5-fluoro-2'-deoxyuridine (502); (j) interactions of ribose ring with pyrimidine in cytidine (503).

Enz-39(C2)

the stacking pattern is modified relative to neutral purine bases, with atoms $N_3$ and $N_7$ of adjacent protonated bases overlapped (Figure 6-8b).

A survey of stacking patterns in base, nucleoside and nucleotide crystal structures suggested that forces between permanent dipoles are only of minor importance for the stabilization of base stacks. Rather it appears that dipole-induced dipole interactions play the major role, with the permanent dipole, predominantly in C=O or C—$NH_2$ groups, superposed over the $\pi$-electronic system of the adjacent base (491).

6.6 Thermodynamic Description of Stacking Interactions

Base stack formation is additive, diffusion controlled, and stabilized by weak interactions. Studies on association of bases and nucleosides in aqueous solution using osmometric techniques (448,504) led early to the conclusion that vertical base stacking occurs and goes beyond the dimeric state (Figure 6-9). Sedimentation equilibrium experiments indicated that the process is reversible with a constant free energy increment for each step, suggesting that addition of a base to another one or to an existing stack is additive and not cooperative and thus follows *isodesmic* behavior (505). The data for purine and pyrimidine nucleosides in aqueous solution in Table 6-6 indicate: (i) that association constants $K$ are characteristic of

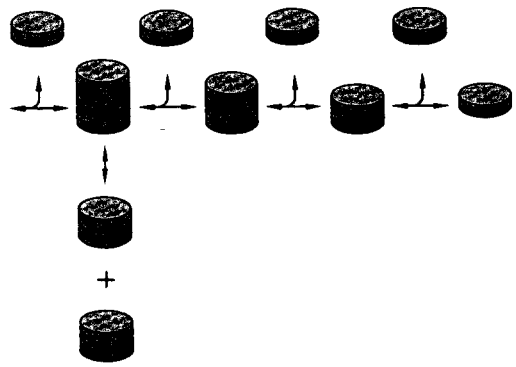

Figure 6-9. Stacking of bases in aqueous medium goes beyond the dimeric state and follows in a broad sense *isodesmic* behavior; i.e., each step is independent and displays the same thermodynamic and kinetic parameters. From (544).

Elazar Rabbani et al.
Serial No. 08/486,053
Filed: June 7, 1995
Page 20 [Exhibit A to Supplemental Amendment to Applicants' January 28, 1999
Amendment Under 37 C.F.R. §1.115 - April 8, 1999]

Table 6-6. Thermodynamic Parameters of Self-association (Stacking) of Nucleosides and Bases in Water [From (448)]

| Compound | K [1/mole] | ΔH [kcal/mole] | ΔS [e.u.] | ΔG [kcal/mole] |
|---|---|---|---|---|
| 6-Methylpurine | 6.7 | −6.0 ± 0.4 | −16 | −1.12 |
| Purine | 2.1 | −4.2 ± 0.2 | −13 | −0.44 |
| Ribosylpurine | 1.9 | −2.5 ± 0.1 | −7 | −0.38 |
| Deoxyadenosine | 4.7 to 7.5 | −6.5 ± 1.0 | −18 | −1.00 |
| Cytidine | 0.87 | −2.8 ± 0.1 | −10 | 0.08 |
| Uridine | 0.61 | −2.7 ± 0.1 | −10 | 0.29 |
| Thymidine | 0.91 | −2.4 ± 0.3 | −9 | 0.06 | weak interactions, (ii) that both enthalpies $\Delta H$ and entropies $\Delta S$ are negative, (iii) that the standard free energy change $\Delta G$ is in the order of the thermal energy $kT$ (0.6 kcal/mole), and (iv) that, in general, methylation of bases leads to moderately increased stacking interactions.

Information regarding the structure of the stacks in aqueous solution has also been provided by NMR measurements (506,507). If two heterocycles aggregate by stacking, the magnetic anisotropy associated with the aromatic ring current in one molecule has a deshielding effect on the protons of the adjacent heterocycle and shifts their resonance signals to higher fields with increasing concentration (Figure 6-10). Relative shifts of base and sugar protons in purine nucleosides indicated that the six-membered pyrimidine ring participates preferentially in stacking rather than the five-membered imidazole fragment, and that the orientation of the heterocycles in a stack depends on the nature of bases, i.e., their amino and keto substituents (448). Because there is no obvious line broadening observed with stack formation, the aggregates build up and break down rapidly on the NMR time scale. Sound absorption techniques indicate that the processes displayed in Figure 6-9 are actually so rapid as to be diffusion controlled (508).

Purine–purine stacks are most stable. Solubility experiments in biphasic systems and NMR data show that stacking interactions between purine and pyrimidine bases follow the trend (509–513)

purine–purine > pyrimidine–purine > pyrimidine–pyrimidine.

If bases are linked to each other in oligo- and polynucleotides, stacking interactions between adjacent bases occur and give rise to stable, single-stranded, helical structures (514). The stabilities of these helices reflect the same trend as given above, with poly(A) mainly helical and poly(U) predominantly random coil at room temperature.

Single-stranded helix formation follows a two-state mechanism. In most cases a simple two-state process (514–522)

helical (stacked) ⇌ random coil (unstacked),

Enz-39(C2)

Elazar Rabbani et al.
Serial No. 08/486,053
Filed: June 7, 1995
Page 21 [Exhibit A to Supplemental Amendment to Applicants' January 28, 1999
    Amendment Under 37 C.F.R. §1.115 - April 8, 1999]

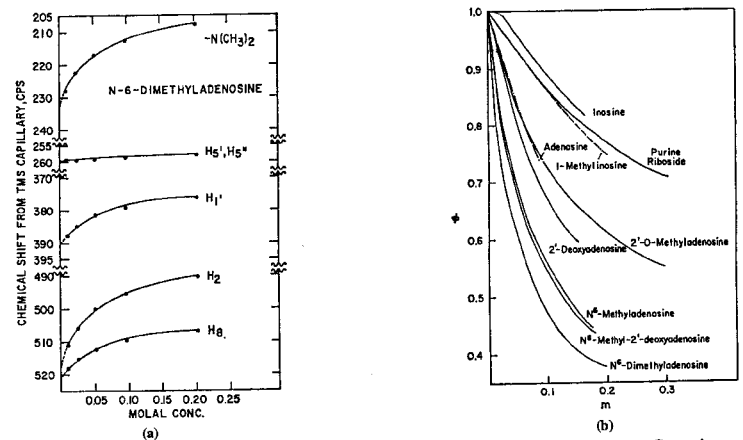

Figure 6-10. Base-stacking visualized by NMR spectroscopy and by vapor pressure osmometry. (a) Dependence of chemical shift of base protons on base concentration yields indication of association constants and structure of formed stacks. $N_6$-Dimethyladenosine in $D_2O$, all spectra taken at 10°C. (b) Osmotic coefficient $\phi$ for various nucleosides in aqueous solution plotted versus molal concentrations ($m$). Curves allow the derivation of association constants and standard free energy of complex formation. Note strong dependence of $\phi$ on methylation of bases. From (506).

Enz-39(C2)

Elazar Rabbani et al.
Serial No. 08/486,053
Filed: June 7, 1995
Page 22 [Exhibit A to Supplemental Amendment to Applicants' January 28, 1999
Amendment Under 37 C.F.R. §1.115 - April 8, 1999]

Table 6-7. Thermodynamic Parameters of Stacking in Some Dinucleoside Phosphates XpY

| Molecule | $\Delta H$ [kcal/mole] | S [cal $K^{-1}mol^{-1}$] | $T_m$ [°C] |
|---|---|---|---|
| ApA[a] | −8.5 ± 0.5 | −28.5 ± 1.5 | 26.2 ± 3 |
| CpC | −8.5 ± 0.5 | −30.0 ± 1.5 | 13.3 ± 5 |
| ApU | −7.3 ± 0.5 | −24.7 ± 1.7 | 22.0 ± 1.1 |
| $m^6$ApU | −7.4 ± 0.3 | −24.8 ± 0.9 | 26.9 ± 0.9 |
| $m_2^6$ApU[b] | −6.5 ± 0.2 | −20.9 ± 0.7 | 36.7 ± 0.8 |
| ApA | −7.2 ± 0.3 | −24.5 ± 0.9 | 21.9 ± 0.9 |
| $m_2^6$Ap$m_2^6$A | −6.7 ± 0.2 | −21.1 ± 0.7 | 44.5 ± 0.8 |

[a] From (522).
[b] From (518).

is sufficient to explain the helix formation behavior of single-stranded oligomers. Thermodynamic parameters for some oligonucleotides are given in Table 6-7. $\Delta H$, $\Delta S$, and $T_m$ for ApU and ApA are virtually identical, and apparently the above given sequence-stacking rule does not apply strictly to oligonucleotides that short. However, the trend is clear for CpC which displays largely reduced stacking properties. As already noted for individual bases in Table 6-6, alkylation increases stacking interactions, indicated by rising $T_m$ values with degree of methylation in Table 6-7.

The earlier proposal of a more complicated mechanism suggested by NMR (516) and kinetic experiments (517) for ApA has been criticized (520). If the more recent circular dichroism and NMR data are considered, then the two-state mechanism appears to be sufficient. These data also show that the overall conformation of sugar moieties in helical oligoribonucleotides is $C_{3'}$-endo. In the helical deoxyribo series, however, $C_{2'}$-endo prevails, with the 3'-terminal nucleotide in rapid $C_{2'}$-endo $\rightleftharpoons$ $C_{3'}$-endo equilibrium (519). This floppy end of a helical oligonucleotide might give rise to a more complex spectrum of conformational states, and the NMR and kinetic data (516,617) should be reconsidered in the light of this new information.

6.7 Forces Stabilizing Base Stacking: Hydrophobic Bonding and London Dispersion Dipoles, π-electron systems, and dipole-induced dipole moments appear to be important in vertical base stacking. In addition, evidence has been presented for the contribution of London dispersion forces (488,489) and for base stacking in aqueous solution, hydrophobic forces also are involved (523,524). How do these forces operate?

Elazar Rabbani et al.
Serial No. 08/486,053
Filed: June 7, 1995
Page 23 [Exhibit A to Supplemental Amendment to Applicants' January 28, 1999
Amendment Under 37 C.F.R. §1.115 - April 8, 1999]

Base stacking is stabilized by entropic contributions: Iceberg water and water cavities. If a base is dissolved in water, the individual solute molecules tend to aggregate and reduce the number of solute–solvent contacts, yielding in extreme cases a two-phase system. This hydrophobic bonding is of particular interest in biological macromolecules because it encourages interactions between nonpolar amino acid side chains or between nucleic acid bases and significantly contributes to secondary and tertiary structure stabilization (525–528). Although widely recognized in a broad sense, hydrophobic forces are still a matter of debate (529).

The aggregation of solute molecules in water has been explained in two ways.

(A) If a (hydrophobic) or nonpolar molecule is dissolved in water, water molecules cluster around its surface. They adopt an "iceberg-like" structure reminiscent of ice clathrates (530) and lose entropy—an unfavorable situation. If the solute molecules aggregate, their surface exposed to water is reduced and structured water molecules are released, resulting in an overall gain in entropy for water which stabilizes the solute complexes (531–533).

(B) A solute molecule entering the water must create a cavity against the surface tension of water. If two or several dissolved solute molecules aggregate, larger cavities are formed and the surface is diminished, leading to a reduction in surface tension which promotes this process (534,535).

Is it possible to distinguish between the two proposals in the case of base stacking? Table 6-6 demonstrates that base stacking in aqueous solution is exothermic and accompanied by negative entropy changes and thus mechanism A seems to be ruled out. However, studies on the system actinomycin:deoxyguanosine, involving the addition of methanol to the aqueous solution, and thermal denaturation experiments on dinucleoside phosphates have indicated that, in fact, a "hidden" positive entropy change occurs with stack formation and that this is, in general, masked by an overall negative entropy change (507,536,537). It appears that mechanism A contributes more significantly to the stacking process than mechanism B, and it is clear from a number of additional experiments that hydrophobic forces are of importance (512,538,539).

Dipolar and London dispersion forces convey stacking specificity. The hydrophobic interactions cannot explain some effects related to specific bases; e.g., purines stack better than pyrimidines and methylation enhances stacking. These individual properties are related to the electronic systems of the bases and are mainly due to London dispersion forces and to interactions between dipoles.

As recognized by London (540), the principal contribution to the ever-effective van der Waals attractive forces between atoms in close proximity resides in electrokinetic interactions between the systems. At any in- Elazar Rabbani et al.
Serial No. 08/486,053
Filed: June 7, 1995
Page 24 [Exhibit A to Supplemental Amendment to Applicants' January 28, 1999
   Amendment Under 37 C.F.R. §1.115 - April 8, 1999]

stant, the electronic charge distribution within atomic groups is asymmetric due to electron fluctuations. Therefore, dipoles created in one group of atoms polarize the electronic system of neighboring atoms or molecules, thus inducing parallel dipoles which attract each other. These forces are additive and decrease with the sixth power of the distance. They are independent of temperature and increase with the product of the polarizabilities of the partner molecules (541). As the bases possess in addition a permanent dipole moment, the two electronic effects, London dispersion and permanent dipoles, combine and lead to appreciable effects which are more pronounced in purine than in pyrimidine bases.

Base-pair hydrogen bonding depends on composition whereas stacking is

Table 6-8. Total Stacking Energies [kcal/mole dimer] for the Ten Possible Dimers in B-DNA Type Arrangement Obtained by Quantum Chemical Calculations[a] [From (542)]

| Stacked dimers | | Stacking energies [kcal/mole dimer] |
|---|---|---|
| ↑C·G↓ / G·C | | −14.59 |
| ↑C·G↓ / A·T | ↑T·A↓ / G·C | −10.51 |
| ↑C·G↓ / T·A | ↑A·T↓ / G·C | −9.81 |
| ↑G·C↓ / C·G | | −9.69 |
| ↑G·C↓ / G·C | ↑C·G↓ / C·G | −8.26 |
| ↑T·A↓ / A·T | | −6.57 |
| ↑G·C↓ / T·A | ↑A·T↓ / C·G | −6.57 |
| ↑G·C↓ / T·A | ↑T·A↓ / C·G | −6.78 |
| ↑A·T↓ / A·T | ↑T·A↓ / T·A | −5.37 |
| ↑A·T↓ / T·A | | −3.82 |

[a] Arrows designate direction of sugar-phosphate chain and point from $C_{3'}$ of one sugar unit to $C_{5'}$ of the next, both carbons attached to the same phosphodiester link.

Elazar Rabbani et al.
Serial No. 08/486,053
Filed: June 7, 1995
Page 25 [Exhibit A to Supplemental Amendment to Applicants' January 28, 1999
Amendment Under 37 C.F.R. §1.115 - April 8, 1999]

influenced by composition and sequence: Results of quantum chemical calculations. Electrostatic forces between stacked bases and base-pairs are intrinsically related to charge distributions and are therefore accessible to quantum chemical calculations. The first rather crude estimations using dipole–dipole approximations were later put on a more refined level employing monopole–monopole interactions, polarization and dispersion interactions and repulsions due to the $1/r^{12}$ term in the Lennard-Jones approach [Eq. (3-5)] (483,484,489,537,542,543).

The data in Table 6-8 for the ten possible combinations of stacks formed by G·C and/or A·T base-pairs were calculated within the frame of B-DNA geometry (Chapter 11). From these (542) and related studies (484) partitioning the total stabilizing energy of base-paired dimers into horizontal (base-pairing) and vertical (base-stacking) components, it becomes clear that horizontal, complementary hydrogen bonding is only composition dependent and more important than vertical stacking which is influenced by both composition and sequence.

As G·C base-pairs are more stable than A·T pairs (Table 6-5), stacked dimers with high G·C content are energetically preferred to those rich in A·T; compare $\begin{vmatrix} C \cdot G \\ G \cdot C \end{vmatrix}$ and $\begin{vmatrix} T \cdot A \\ A \cdot T \end{vmatrix}$ which differ by 8 kcal/mole dimer. The influence of stacking energy is expressed in the general sequence dependences showing that $\begin{vmatrix} 5'\text{pyrimidine·purine}_{3'} \\ 3'\text{purine·pyrimidine}_{5'} \end{vmatrix}$ is more stable than $\begin{vmatrix} 5'\text{purine·pyrimidine}_{3'} \\ 3'\text{pyrimidine·purine}_{5'} \end{vmatrix}$ See, for instance, $\begin{vmatrix} C \cdot G \\ G \cdot C \end{vmatrix}$ and $\begin{vmatrix} G \cdot C \\ C \cdot G \end{vmatrix}$ which differ by about 5 kcal/mole dimer (Table 6-8). The origin of this energy–sequence correlation becomes clear if the geometries of the stacking overlaps displayed in Figure 9-6 are considered. In the alternating purine, pyrimidine sequences, overlap between adjacent bases in a stack is governed by the sequence $\begin{vmatrix} 5'\text{pyrimidine} \\ 3'\text{purine} \end{vmatrix}$ or $\begin{vmatrix} 5'\text{purine} \\ 3'\text{pyrimidine} \end{vmatrix}$ and is very different from the overlap observed in base-paired dimers containing only purine or only pyrimidine bases in one strand.

It should be stressed that the data in Table 6-8 consider only molecules *in vacuo* and do not take into account hydrophobic interactions which, however, contribute significantly to stacking interactions. In experiments discussed in the next section, base-pairing and stacking interactions in aqueous solutions are obtained as total contributions to oligo- and polynucleotide helix stability.

Elazar Rabbani et al.
Serial No. 08/486,053
Filed: June 7, 1995
Page 26 [Exhibit A to Supplemental Amendment to Applicants' January 28, 1999
    Amendment Under 37 C.F.R. §1.115 - April 8, 1999]

6.8 Formation and Breakdown of Double-Helix Structure Show Cooperative Behavior A helix with the pitch as basic repeating motif may be considered as if it were a one-dimensional, crystalline lattice. A formal analogy of helical and crystalline order is reflected in physical properties: both break down suddenly at a certain (melting) temperature and both grow and propagate after a nucleus (seed) has been formed.

Cooperative zipper mechanism of helix formation requires three-base-pair nucleus. As shown schematically in Figure 6-11 for double-helix formation between poly(U) and poly(A), the first step is association of a single A·U base-pair with a stability constant expressed as the product of nucleation parameter $\beta$ ($10^{-3}$ liters/mole), and chain growth parameter $s$ (around 10 at 0°C and 1 at melting temperature) which were both determined by relaxation kinetics. This first, isolated base-pair is rather unstable due to the influence of $\beta$ but addition of another, neighboring and stacked base-pair follows with stability constant $s$, not diminished by this parameter $\beta$. A third base-pair is stacked on top of the first two and creates a suitable nucleus from which further addition of stacked base-pairs leads to stepwise construction of a helix just as a zipper is closed (544).

The energy profile of this process is schematically illustrated in Figure 6-12. Formation of the initial, isolated base-pair is unfavorable and gives

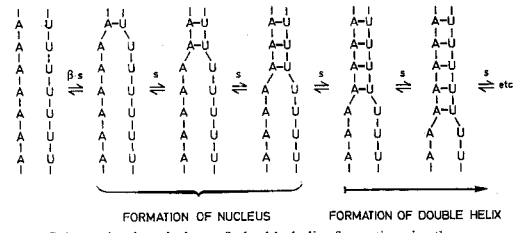

Figure 6-11. Schematic description of double-helix formation in the case of oligo(A)·oligo(U). In this system, helix growth parameter $s$ is about 10 at 0°C and 1 at the melting temperature. Nucleation parameter $\beta$, $10^{-3}$ liters/mole, diminishes stability constant $K = \beta \cdot s$ of primary base-pair formation but does not influence formation of additional, stacked base-pairs which form cooperatively with $K = s$ according to a *linear Ising model*. In constrast to the *isodesmic model* for base stacking (Figure 6-9), where each step is independent of the other, in the *cooperative process* described by the Ising model, base-pair formation and stacking are influenced by the next neighbors, except for the very first base–base association. After (544).

Elazar Rabbani et al.
Serial No. 08/486,053
Filed: June 7, 1995
Page 27 [Exhibit A to Supplemental Amendment to Applicants' January 28, 1999
    Amendment Under 37 C.F.R. §1.115 - April 8, 1999]

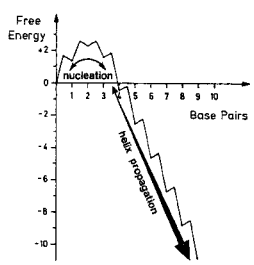

Figure 6-12. After the unfavorable positive free energy contribution in the nucleation process is overcome, the free energy for additional steps becomes negative and the helix grows spontaneously. Relative total free energy ($\Delta G$) of helix formation in arbitrary units is plotted as a function of the number of consecutive, stacked base-pairs assembled into a helical array. From (544).

positive contributions to free energy. After three consecutive, stacked base-pairs have created a nucleus which can still dissociate easily into its components, addition of new base-pairs stacked to the nucleus leads to favorable, negative contributions to free energy. From then on, growth of the double helix is spontaneous, due mainly to geometrical constraints of

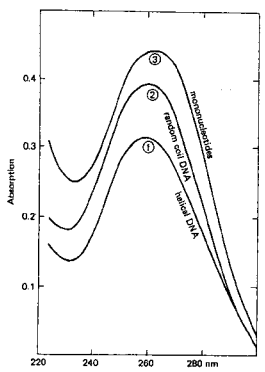

Figure 6-13. Ultraviolet absorption spectra of DNA in native double helical (1) and denatured random coil (2) states and spectrum of individual, monomeric, unstacked nucleotides of the same concentration as in native DNA (3). In denatured state (2), bases are still considerably stacked. From (185).

Elazar Rabbani et al.
Serial No. 08/486,053
Filed: June 7, 1995
Page 28 [Exhibit A to Supplemental Amendment to Applicants' January 28, 1999 Amendment Under 37 C.F.R. §1.115 - April 8, 1999]

the sugar–phosphate backbone which are implied by the stereochemistry of the nucleotide unit which, in its preferred conformation, is preformed to suit this purpose. Beyond that, base-pair stacking and hydrogen-bonding interactions act along the same line and these effects taken together are responsible for the cooperative behavior of nucleic acid helix formation and break down (melting).

Melting temperature $T_m$ characterizes a double helix. Base stacking is accompanied by reduction in UV absorption (hypochromicity, Figure 6-13), so the UV spectrum is a convenient monitor of the formation and breakdown of double helices. If the temperature of a solution containing double-helical DNA (or RNA) is slowly raised, UV absorption increases suddenly at a certain temperature because ordered double helices dissociate. The midpoint of transition is called the "melting temperature" or $T_m$. This process is pictured for oligo(A)·oligo(U) double helices of different chain lengths in Figure 6-14. It is obvious that, with increasing chain

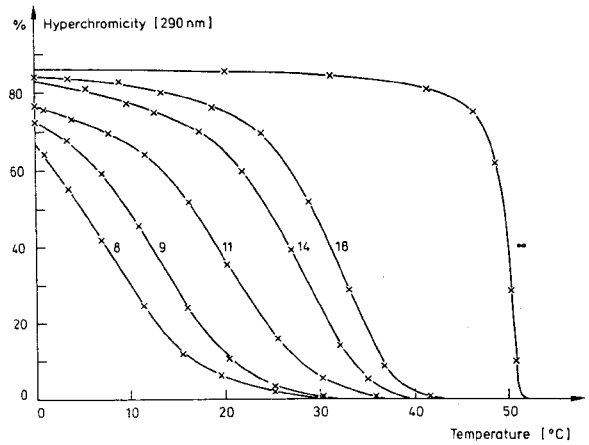

Figure 6-14. Melting profiles of cooperative helix⇌coil transition for oligo(A) oligo(U) double helices of various chain lengths, from 8 to ∞ nucleotides. Melting points $T_m$ correspond to 50% transition and are around 49°C for long poly(A) · poly(U) duplexes. Plotted are changes in ultraviolet absorption at 290 nm in the form of hyperchromic effects defined as $100 \times (E_T - E_C) \cdot E_C$, where $E_T$ = absorption at temperature $T$, $E_C$ = absorption at 100% coil form. Concentrations are 5 to 11.3 m$M$ oligonucleotides, 50 m$M$ sodium cacodylate buffer at pH 6.9. From (545).

Enz-39(C2)

length, $T_m$ increases and the slope at the point of inflection ($T_m$) becomes steeper, synonymous with enhanced cooperativity (545–547).

Helix–coil transitions for double-helical structures are approximately an all-or-none process: Helix⇌Coil. As shown in Figure 6-15, a population analysis of the system $A(pA)_{17} \cdot U(pU)_{17}$ at various temperatures yields exclusively either dissociated, coiled monomers or fully integrated double helices with only the terminal base-pairs in a rapid dissociation–recombination process.

The melting temperatures of double-helical nucleic acids increase not

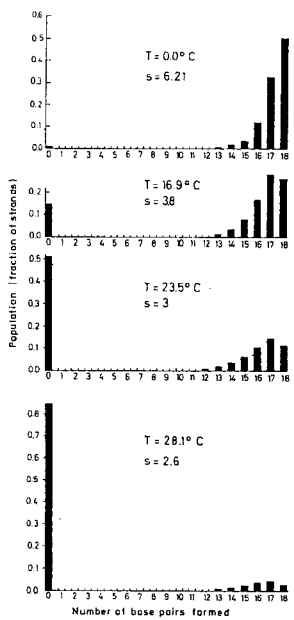

Figure 6-15. Population analysis for the system $A(pA)_{17} \cdot U(pU)_{17}$ at different temperatures. Product of [(nucleation parameter $\beta$) × (concentration c)] used in this analysis is $\beta \cdot c = 10^{-7}$. Note that base-pairs at ends of the helix open and close easily, giving rise to a distribution of helices with 13 to 18 base-pairs but helices with 1 to 12 base-pairs are practically not observed; they either dissociate or form helices with 13 to 18 base-pairs. From (548).

Elazar Rabbani et al.
Serial No. 08/486,053
Filed: June 7, 1995
Page 30 [Exhibit A to Supplemental Amendment to Applicants' January 28, 1999
Amendment Under 37 C.F.R. §1.115 - April 8, 1999]

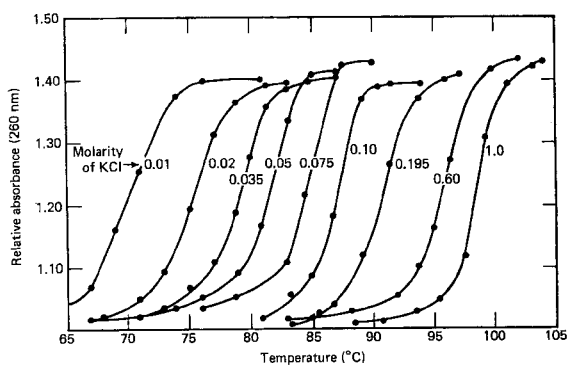

Figure 6-16. Dependence of thermal denaturation of *D. pneumoniae* (R-36A) DNA on ionic strength. Various KCl concentrations in citrate buffer, pH 7.0. From (549).

only with their lengths but also with the ionic strength of the medium and with the GC/AT ratio of the polynucleotide (Figures 6-16,6-17). As the composition linearly influences the melting temperature to a good approximation, it can be evaluated from the $T_m$ value. Because of this dependence of melting behavior on nucleotide composition, it follows that in a double-helical DNA or RNA with random sequence, A–T(U)-rich regions should melt at lower temperatures than G–C-rich regions (Figure 6-18). This gives rise to local breakdown of helical order (550). It leads to the observed broad relaxation spectrum of the melting process (544,550). Differential melting curves, in which the differential change of absorption with temperature, $\Delta A/\Delta T$, is plotted versus temperature, $T$, display a rugged profile with a multitude of maxima which can be deconvoluted to yield individual double-helical domains melting at similar, yet significantly distinct temperatures and indicative of different GC/AT(U) content (551–554) (Figure 6-19).

Analysis of a number of such profiles produced the "stability matrix" for stacked, base-paired dinucleotides in B-DNA geometry which gives $T_m$ values for base-paired doublets at certain conditions, Table 6-9a. From these data, the melting temperature $T_m$ of a DNA double helix of any sequence can be estimated. Some examples are entered in Table 6-9b. If melting temperatures of duplexes calculated on the basis of Table 6-9 are plotted against stacking energies obtained by quantum chemical calculations (Table 6-8), it is striking to find that a linear correlation emerges (Figure 6-20). Experimental and theoretical approaches form a consistent picture although the theoretical work neglects contributions due to hydro- Enz-39(C2)

Elazar Rabbani et al.
Serial No. 08/486,053
Filed: June 7, 1995
Page 31 [Exhibit A to Supplemental Amendment to Applicants' January 28, 1999
Amendment Under 37 C.F.R. §1.115 - April 8, 1999]

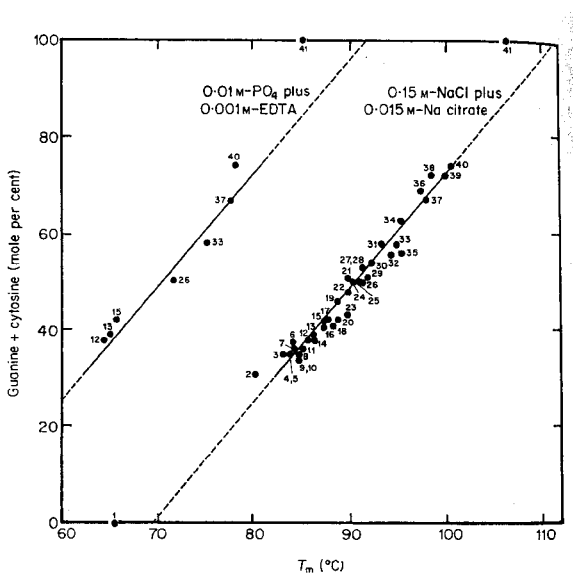

Figure 6-17. Dependence of melting temperature $T_m$ on guanine + cytosine (G + C) content of various samples of DNA obtained from different sources. DNA was dissolved in 0.15 $M$ NaCl + 0.015 $M$ Na-citrate, pH 7.0. Points 1 and 41, for poly(dA-dT) and poly(dG-dC), fall off the least-squares line which is described analytically by $T_m$ = 69.3 + 0.41 (%C). From (549).

phobic effects, steric constraints, positive ions around phosphate groups, hydration, etc., which, to a certain extent, seem to counterbalance each other.

Using oligo-ribonucleotides with defined sequence as model compounds, thermodynamic parameters for adding or subtracting one base-pair to or from an existing helix were derived (554–557). Table 6-10 predicts that depending on nucleotide sequence and composition, RNA duplexes exhibit the following trend in helix stability: poly(G)·poly(C) > poly(G-C)·poly(G-C) > (double helix with random sequence) > poly(A-U)·poly(A-U) > poly(A)·poly(U). The A/U case is surprising because in the DNA series, poly(dA)·poly(dT) is more stable than the alternating copolymer poly(dA-dT)·poly(dA-dT) (558). For the latter, formation of short hair- Elazar Rabbani et al.
Serial No. 08/486,053
Filed: June 7, 1995
Page 32 [Exhibit A to Supplemental Amendment to Applicants' January 28, 1999
         Amendment Under 37 C.F.R. §1.115 - April 8, 1999]

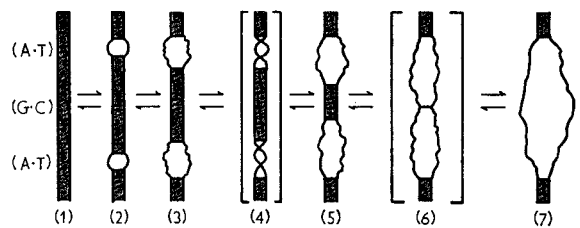

Figure 6-18. Scheme describing processes involved in DNA or RNA double-helix de- and renaturation. A–T-rich regions melt first, giving rise to states (2) and (3). In (4), additional base-pairs are opened and the twist is taken up in coil regions. From (550).

pin loops with reduced thermal stability has been invoked to explain the overall low $T_m$. Since the RNA analog is also able to produce such hairpins (as is known from tRNA), it appears that the differences in stability are correlated not with composition but rather with helix structure, the deoxy analogs preferring B- and D-type helices whereas all ribo-polynucleotides can only occur in the A-form (Chapter 9).

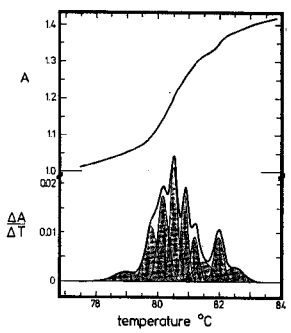

Figure 6-19. Melting profile of DNA (top) and its first derivative dA/dT (bottom). The latter curve is deconvoluted into nine individual peaks characterized by temperature, amplitude, and breadth. $A$ indicates UV absorption at 260 nm; dA/dT or ΔA/ΔT are first derivatives with respect to temperature $T$. These curves are simulated; for some realistic data see Ref. (557).

Elazar Rabbani et al.
Serial No. 08/486,053
Filed: June 7, 1995
Page 33 [Exhibit A to Supplemental Amendment to Applicants' January 28, 1999 Amendment Under 37 C.F.R. §1.115 - April 8, 1999]

Table 6-9. Prediction of DNA Double Helix Stability from Base Sequence [From (555)]

(A) Stability Matrix for Nearest-Neighbor Stacking in Base-Paired Dinucleotides in B-DNA Geometry[a]:

| 5' | 3' | | | |
|---|---|---|---|---|
|  | A | T | G | C |
| T | 36.73 | 54.50 | 54.71 | 86.44 |
| A | 54.50 | 57.02 | 58.42 | 97.73 |
| C | 54.71 | 58.42 | 72.55 | 85.97 |
| G | 86.44 | 97.73 | 85.97 | 136.12 |

[a] Numbers give $T_m$ values in °C at 19.5 m$M$ Na$^+$.

(B) $T_m$ Values Predicted with This Matrix for a Collection of Synthetic DNA Polymers with Defined Sequence:

| Polynucleotide | $T_m$(°C) Experimental[a] | Calculated[b] | Difference[c] |
|---|---|---|---|
| Poly(dA-dT)·poly(dA-dT) | 45.0 | 46.9 | −1.9 |
| Poly(dA-dA-dT)·poly(dA-dT-dT) | 49.2 | 49.4 | −0.2 |
| Poly(dA)·poly(dT) | 53.0 | 54.5 | −1.5 |
| Poly(dG-dA-dA)·poly(dT-dT-dC) | 64.5 | 66.5 | −2.0 |
| Poly(dG-dT-dA)·poly(dT-dA-dC) | 66.8 | 64.3 | 2.5 |
| Poly(dA-dA-dC)·poly(dG-dT-dT) | 70.2 | 69.0 | 1.2 |
| Poly(dG-dA)·poly(dT-dC) | 71.3 | 72.4 | −1.1 |
| Poly(dG-dA-dT)·poly(dA-dT-dC) | 72.0 | 66.1 | 5.9 |
| Poly(dG-dG-dA)·poly(dT-dC-dC) | 76.3 | 76.9 | −0.6 |
| Poly(dG-dT)·poly(dA-dC) | 77.4 | 76.2 | 1.2 |
| Poly(dG)·poly(dC) | 87.8 | 86.0 | 1.8 |
| Poly(dG-dC)·poly(dG-dC) | 99.2 | 104.3 | −5.1 |

[a] Experimental melting temperatures at various ionic strengths are interpolated to 19.5 m$M$ Na$^+$.
[b] Calculated from values in Table 6-9(A) and nearest-neighbor frequencies in each polymer.
[c] $T_m$ (experimental) − $T_m$ (calculated).

Hairpins, bulges, and loops. In addition to next-neighbor stabilization in RNA double helices, contributions due to formation of hairpin loops, bulges, and interior loops have been evaluated (557–561) (Table 6-10, Figure 6-21). The data suggest that interior loops and bulges are more stable than hairpin loops which are optimum for six nonbonded bases.

It should be stressed that in a double-helical DNA or RNA structure, base-pairs at the termini and base-pairs within the helical stem can both potentially open. The expected frequency for the latter process is rather Elazar Rabbani et al.
Serial No. 08/486,053
Filed: June 7, 1995
Page 34 [Exhibit A to Supplemental Amendment to Applicants' January 28, 1999
    Amendment Under 37 C.F.R. §1.115 - April 8, 1999]

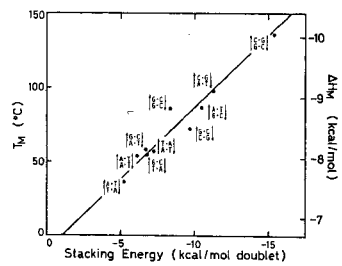

Figure 6-20. Correlation diagram between experimental melting temperatures $T_m$ (Table 6-9) and theoretically evaluated stacking energies (Table 6-8) of base-paired dinucleotides in B-DNA geometry. Note that two different approaches to the same problem yield a satisfactory correlation with a correlation coefficient of 0.97. Stacking energies for dinucleotide duplexes entered in this plot differ slightly from data in Table 6-8 because different results given in Ref. (536) were used. From (555).

low and has been evaluated from measurements of oligoribonucleotide double-helical complexes (563,564) (Table 6-11). The G–C base-pair is, in general, more stable by a factor 100 than an A–U pair, and the flanking base-pairs play an important, additional role. On the basis of these data, one can estimate that in a double-helical RNA of random sequence and one million base-pairs long, at 25°C about 10 G–C and 500 A–U pairs are in non-hydrogen-bonded, unstacked configuration. This description suggests that double-helical nucleic acids should not be considered as static columns but rather as flexible, "breathing" entities, in harmony with chemical modification experiments (563).

6.9 Base-Pair Tautomerism and Wobbling: Structural Aspects of Spontaneous Mutation and the Genetic Code If, in living organisms, base-pairing always occurred in a strict Watson–Crick sense, life on this planet would not display the great variety of species in fauna and flora which are due to mutations. Altered genetic information is given to daughter generations via replication and is passed on to protein biosynthesis via transcription and translation as described schematically in Figure 6-22.

Replication, transcription, translation, and the genetic code. In all three processes, base–base recognition by means of Watson–Crick pairing is Elazar Rabbani et al.
Serial No. 08/486,053
Filed: June 7, 1995
Page 35 [Exhibit A to Supplemental Amendment to Applicants' January 28, 1999
   Amendment Under 37 C.F.R. §1.115 - April 8, 1999]

Table 6-10. Experimentally Determined Free Energies at 25°C for RNA Double Helical and Looped Structures[a] [From (557)]

| Base paired regions | $\Delta G$(kcalorie) ± 10% |
|---|---|
| $-\overrightarrow{A-A}-$ / $-\underleftarrow{U-U}-$ | −1.2 |
| $-\overrightarrow{A-U}-$  $-\overrightarrow{U-A}-$ / $-\underleftarrow{U-A}-$ ' $-\underleftarrow{A-U}-$ | −1.8 |
| $-\overrightarrow{A-C}-$  $-\overrightarrow{C-A}-$  $-\overrightarrow{A-G}-$  $-\overrightarrow{G-A}-$ / $-\underleftarrow{U-G}-$ ' $-\underleftarrow{G-U}-$ ' $-\underleftarrow{U-C}-$ ' $-\underleftarrow{C-U}-$ | −2.2 |
| $-\overrightarrow{C-G}-$ / $-\underleftarrow{G-C}-$ | −3.2 |
| $-\overrightarrow{G-C}-$  $-\overrightarrow{G-G}-$ / $-\underleftarrow{C-G}-$ ' $\underleftarrow{C\ C}-$ | −5.0 |
| $-\overrightarrow{G-U}-$ / $-\underleftarrow{U-G}-$ | −0.3 |
| $-\overrightarrow{G-X}-$  $-\overrightarrow{X-G}-$ / $-\underleftarrow{U-Y}-$ ' $-\underleftarrow{U-Y}-$ | 0 |

| Unbonded regions | $\Delta G$(kcalorie) ± 1 kcalorie |
|---|---|
| Number of bases unbonded | Interior loops |
| 2–6 | +2 |
| 7–20 | +3 |
| m (>20) | 1 + 2 log m |
| | Bulge loops |
| 1 | +3 |
| 2–3 | +4 |
| 4–7 | +5 |
| 8–20 | +6 |
| m (>20) | 4 + 2 log m |

| | Hairpin loops | |
|---|---|---|
| | Closed by G·C | Closed by A·U |
| 3 | +8 | >8 |
| 4–5 | +5 | +7 |
| 6–7 | +4 | +6 |
| 8–9 | +5 | +7 |
| 10–30 | +6 | +8 |
| m (>30) | 3.5 + 2 log m | 5.5 + 2 log m |

[a] The free energies ($\Delta G$) for the base-paired regions refer to the free energy of adding a base-pair to a pre-existing helix; therefore the magnitude depends on the sequence of two base-pairs.

Enz-39(C2)

Elazar Rabbani et al.
Serial No. 08/486,053
Filed: June 7, 1995
Page 36 [Exhibit A to Supplemental Amendment to Applicants' January 28, 1999
Amendment Under 37 C.F.R. §1.115 - April 8, 1999]
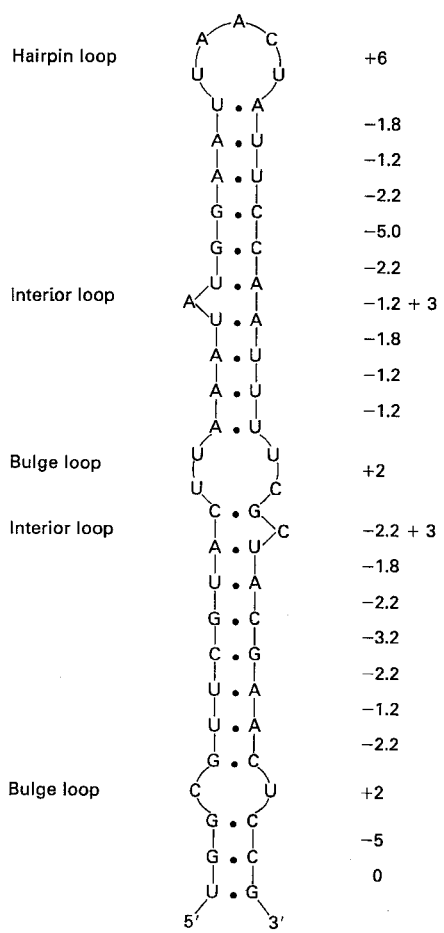
Figure 6-21. Application of data entered in Tables 6-10 and 6-11 to evaluate a possible secondary structure for a 55-nucleotide fragment from R17 virus (557). Overall $\Delta G$ at 25°C is $-21.8$ kcal/mole. For slightly different, revised data see (556).
Enz-39(C2)

Elazar Rabbani et al.
Serial No. 08/486,053
Filed: June 7, 1995
Page 37 [Exhibit A to Supplemental Amendment to Applicants' January 28, 1999
Amendment Under 37 C.F.R. §1.115 - April 8, 1999]

Table 6-11. Transient Opening Probabilities for
A·U and G·C Base–Pairs in Double Helical RNA
[From (561)]

| Arrangement | ΔG for opening central pair (25°C, kcal/mole) | Probability of opening |
|---|---|---|
| G–G–G<br>C–C–C | 7.5 | $0.3 \times 10^{-5}$ |
| G–G–A<br>C–C–U | 6.75 | $1.2 \times 10^{-5}$ |
| A–G–G<br>U–C–C | 6.75 | $1.2 \times 10^{-5}$ |
| A–G–A<br>U–C–U | 6.0 | $4.2 \times 10^{-5}$ |
| A–A–A<br>U–U–U | 4.0 | $120 \times 10^{-5}$ |
| A–A–G<br>U–U–C | 4.15 | $100 \times 10^{-5}$ |
| G–A–A<br>C–U–U | 4.15 | $100 \times 10^{-5}$ |
| G–A–G<br>C–U–C | 4.3 | $70 \times 10^{-5}$ | crucial and leads to direct copying of DNA (*replication*) and to transformation of sequence in DNA into corresponding sequence (*transcription*) in messenger RNA (mRNA). In *translation*, the information contained in the mRNA nucleotide sequence is translated, at the ribosomal machinery, into polypeptide amino acid sequence with the amino acid carrying tRNA serving as mediator (564). According to its amino acid specificity, the tRNA molecule consists of an anticodon of three nucleotides (triplet) which recognizes a complementary codon on the mRNA and, following the rules implied by the genetic code (Figure 6-23), incorporates amino acids sequentially into a growing polypeptide chain, with mRNA as guideline read off from the 5'- to 3'-terminus.

Mutations can occur if non-Watson-Crick base-pairs are formed. Let us look first at DNA replication. In this process two types of simple spontaneous substitution mutations can occur: (i) *transitions*, where a purine is replaced by another purine or a pyrimidine is replaced by another pyrimidine; and (ii) *transversions*, where a purine is exchanged for a pyrimidine or vice versa (565) (Figure 6-24). Experimentally observed mutation rates are of the order $10^{-8}$ to $10^{-11}$ per base-pair synthesized (566) and represent those cases in which noncomplementary base-pairs in the strict Watson-Crick sense have escaped two DNA polymerase checking processes. This Elazar Rabbani et al.
Serial No. 08/486,053
Filed: June 7, 1995
Page 38 [Exhibit A to Supplemental Amendment to Applicants' January 28, 1999 Amendment Under 37 C.F.R. §1.115 - April 8, 1999]

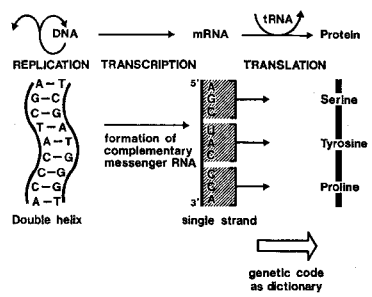

Figure 6-22. Schematic, simplified description of the central dogma in molecular genetics (584). Double-helical DNA is replicated and passed on from one generation to the next. In the DNA nucleotide sequence, information on amino acid sequence in protein is encoded. In order to synthesize protein, DNA is transcribed into complementary messenger RNA (mRNA) the sequence of which, at the ribosome, is translated into a protein sequence, with one nucleotide triplet coding for one amino acid according to the rules given by the genetic code (Figure 6-23). Transfer RNA, as adapter molecule, carries an anticodon complementary to the mRNA codon and an amino acid specific for that anticodon.

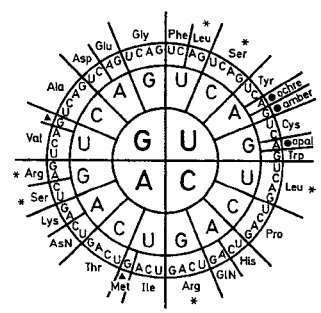

Figure 6-23. The genetic code displayed in radial form. The codons are to be read from the center (5') outward (3') and represent mRNA triplets coding for amino acids entered at the periphery. The last (3'-terminal) base is redundant (degenerate) except for amino acids Trp and Met whereas the first two bases are specific. Amino acids marked * appear twice, dots ● and triangles ▲ indicate terminator and starting codons, respectively. From (585).

Enz-39(C2)

Elazar Rabbani et al.
Serial No. 08/486,053
Filed: June 7, 1995
Page 39 [Exhibit A to Supplemental Amendment to Applicants' January 28, 1999
    Amendment Under 37 C.F.R. §1.115 - April 8, 1999]

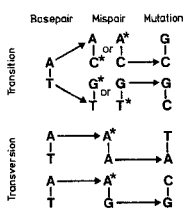

Figure 6-24. Pathways for spontaneous substitution mutations of A–T base-pairs caused by *transitions* and *transversions* (566). A comparable scheme can be drawn for G–C pairs. Both mutation processes are explained with rare tautomeric imino and enol forms of bases indicated by *. In transversion, purine–purine base-pairs with one base in *syn* conformation, as described in Figure 6-25, are involved. Pyrimidine–pyrimidine pairs are unlikely to pass enzymatic checking mechanisms because they have too short geometry. After (570).

enzyme travels along DNA in 5'→3' direction, takes up nucleoside triphosphates, and incorporates them into a newly synthesized DNA, complementary to the original DNA (567). Each step in synthesis is tested for correctness in a subsequent proofreading step, and the newly added nucleotide is excised by a counterrunning 3'→5' exonuclease if found erroneous (568,569).

Recalling Section 5.4, we find that bases can occur in rare tautomeric enol and imino forms at concentrations of $10^{-4}$ to $10^{-5}$ moles/liter. This can give rise to the non-Watson–Crick mispairs displayed in Figure 6-25. If in both synthesizing and proofreading steps, which are independent of each other, rare tautomeric forms do occur and do mimic Watson–Crick geometry, they are not detected and pass the enzymatic tests unhindered.

For an assessment of overall mutation rate, therefore, the two individual tautomer concentrations are multiplied, resulting in $10^{-4} \times 10^{-4}$ to $10^{-5} \times 10^{-5}$ or $10^{-8}$ to $10^{-10}$ mutations per newly synthesized DNA, in agreement with experiment (570).

Transversions follow a different scheme than transitions. For transversions, a different mechanism has been proposed involving purine–purine instead of purine–pyrimidine mispairs in order to explain the mutations described in Figure 6-24. Because "standard" purine–purine base-pairs are longer than purine–pyrimidine pairs and would not be tolerated by the synthesizing and proofreading apparatus, an *anti→syn* conversion of the new, incoming nucleoside triphosphate was postulated to allow for a "normal-size" purine–purine pair which additionally requires rare tautomeric forms of the bases (Figure 6-25). The *anti →syn* rotation will decrease the probability of mutations by another factor of $10^{-1}$ to $10^{-2}$, yielding $10^{-10}$ to $10^{-12}$ transversions per newly incorporated nucleotide, again in harmony with experimental findings (570,571).

Enz-39(C2)

Elazar Rabbani et al.
Serial No. 08/486,053
Filed: June 7, 1995
Page 40 [Exhibit A to Supplemental Amendment to Applicants' January 28, 1999
    Amendment Under 37 C.F.R. §1.115 - April 8, 1999]

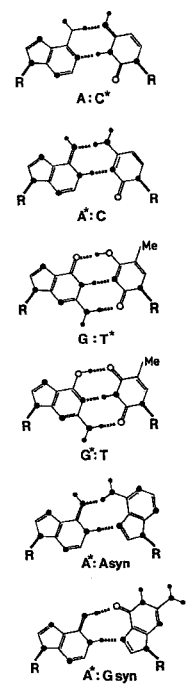

Figure 6-25. Some tautomeric non-Watson–Crick base-pairs likely to be involved in the mutation schemes described in Figure 6-24. For further base-pairs, see (570). Bases in rare tautomeric forms are marked *.

"Wobbling" of bases in mutations and in tRNA–mRNA recognition. The explanation of spontaneous substitution mutations of DNA with rare tautomeric forms of the bases is attractive and encompasses even chemical mutations due to incorporation of 5-bromouracil and 2-aminopurine. On the other hand, mutation can, at least in some cases like G–T mispairing, be accounted for by misadjustment of juxtaposed bases without invoking rare tautomeric forms. This "wobbling" due to steric misalignment of bases in a base-pair was proposed by Crick for the translation process (572) and was later verified experimentally (573–576).

Enz-39(C2)

Elazar Rabbani et al.
Serial No. 08/486,053
Filed: June 7, 1995
Page 41 [Exhibit A to Supplemental Amendment to Applicants' January 28, 1999
    Amendment Under 37 C.F.R. §1.115 - April 8, 1999]

The "wobble" theory was put forward in order to explain redundancies in the genetic code which relates amino acid sequence of newly synthesized polypeptide with nucleotide sequence in mRNA. In a series of experiments (577), it was demonstrated that a nucleotide triplet in mRNA (a codon) is recognized by a complementary triplet in tRNA (an anticodon) carrying, attached to its 3' terminus, the anticodon-specific amino acid to be incorporated into the growing polypeptide chain. Because 20 amino acids are coded by triplets of the four different nucleotides A,U,G,C, i.e., by $4^3 = 64$ possible words, a degeneracy is programmed in this translation code. If regarded in the reading direction from the 5' to the 3' terminus in mRNA, the first two letters of a codon are fixed according to the amino acid incorporated but the third one is variable (degenerate) and can include from one to four different bases (Figure 6-23).

The question whether each of the 64 possible codons has one partner tRNA or whether one particular tRNA can recognize several codons with the same first two letters but different letters in the third place was resolved in favor of the latter, and supported the wobble hypothesis.

According to this hypothesis, three base-pairs are formed between mRNA codon and tRNA anticodon. The first two of these are of the standard Watson–Crick type but in the third position, deviations are allowed to occur and consist of pairing between:

| Base on the tRNA anticodon in third (3') position | Bases recognized on the mRNA codon | |
|---|---|---|
| | Standard Watson–Crick | Wobble |
| U | A | G |
| C | G | |
| G | C | U |
| I | C | U,A |

It is remarkable that thus far no tRNA could be found with an A in the third (wobble) position of the anticodon (578), probably due to deamination after synthesis.

Some "wobble" base-pairs are more likely to occur than others. In the wobble hypothesis, pairings between pyrimidine bases like U–U and U–C (base-pairs XVI and XVIII in Figure 6-1) were considered improbable because the distance between glycosyl links in these base-pairs, ~8.5 Å, is about 2 Å shorter than the 10.6 Å distance in a standard Watson–Crick base-pair. The overall Watson–Crick geometry is probably essential because base-paired codon–anticodon triplets will stack in a helical arrangement and large deviations from Watson–Crick geometry could not be tolerated (579) (Section 15.7). This raises questions about the long A–I "wobble" base-pair because of the 12.8 Å separation between glycosyl $C_{1'}$ atoms. In a more recent proposal (580), an $A-I_{syn}$ base-pair as found in Enz-39(C2)

Elazar Rabbani et al.
Serial No. 08/486,053
Filed: June 7, 1995
Page 42 [Exhibit A to Supplemental Amendment to Applicants' January 28, 1999
Amendment Under 37 C.F.R. §1.115 - April 8, 1999]

the 9-ethyl-8-bromoadenine·9-ethyl-8-bromohypoxanthine complex (581) was advocated; its overall dimensions imitate Watson–Crick geometry.

The wobble base-pairs proposed in (572) are displayed and compared with standard A–U Watson–Crick base-pairs in Figure 6-26. They are all linked by two cyclic hydrogen bonds, but their geometry is different from that of standard pairs because the glycosyl $C_{1'}$–N bonds do not obey dyad symmetry and the isomorphism of A–U and G–C base-pairs is lost.

Evidence for the "wobble" base-pairs comes not only from the translation process: The G–U base-pair was directly visualized in the acceptor stem of $tRNA_{yeast}^{Phe}$ (Chapter 15). It probably accounts for the stability of the poly(G)·poly(U) double helix (582) and was found to approximate, in a complementary double-helical oligonucleotide, an A–U base-pair in stabilizing efficiency (583). As for the long A–I base-pair, it could be verified in the all-purine double-helix poly(A)·poly(I) (Chapter 13).

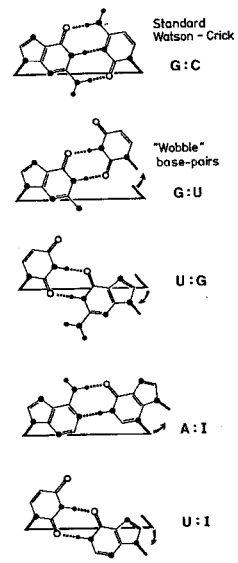

Figure 6-26. Comparison of Watson–Crick and "wobble" base-pairs. Deviations from standard geometry are indicated by colored arrows. For more base-pairs involving not wobbling but enol/imino tautomerism, see (580).

Elazar Rabbani et al.
Serial No. 08/486,053
Filed: June 7, 1995
Page 43 [Exhibit A to Supplemental Amendment to Applicants' January 28, 1999
Amendment Under 37 C.F.R. §1.115 - April 8, 1999]

Summary

This chapter covers associative forces between bases which are greatly responsible for the stability of a double-helical array. Most important are hydrogen-bonded base-pairs between like (homo) and different (hetero) bases which can be arranged in 28 different ways. Among the hetero pairs, only those with Watson–Crick geometry lead to regular double-helical structures because they are isomorphous. The A–T(U) and G–C base-pairs are pseudosymmetrical; a twofold rotation axis relates glycosyl links (and attached sugar–phosphate backbones) but not individual base-pair atoms. Hydrogen-bonding interactions between bases in a pair are specific and indicate electronic complementarity, with G–C more stable than A–U(T) and homo or other hetero base-pairs less favored. In crystal structures of nucleic acid constituents and double-helical arrays, bases form vertical stacks which show rather specific patterns, exocyclic groups ($C=O$ and $C-NH_2$), or ring nitrogen located over the heterocycle of the adjacent base. Stacking interactions are mainly due to dispersion and dipole-induced dipole forces and hydrophobic bonding. In double-helical structures, formation and breakdown display cooperative characteristics, associated with geometrical constraints due to sugar–phosphate backbone and interbase interactions due to stacking and base-pairing.

The strict Watson–Crick base-pairing scheme is systematically violated in translation processes in tRNA anticodon–codon recognition where "wobble" base-pairs are allowed. This natural disregard of Watson–Crick base-pairing is not only found in translation; in DNA replication it leads to mutation, with mutation rates explicable by the occurrence of tautomeric imino and enol forms and by *syn/anti* conformers of purine nucleotides.

In the preferred embodiment, one or more washing steps are used to remove the excess probe strand which is ionically associated with the solid matrix. The washing steps are not necessary, but are preferred for greater accuracy, in order to avoid any energy transfer between the capture intercalator and the probe strand, thus leading to a production of non-specific signal. The washing steps are carried out under the same conditions as used for hybridization. A suitable energy donor, which is a different intercalating compound, is added in a room temperature phosphate buffer (>10 millimolar) following the washes. The energy acceptor is a lanthanide metal. It can be any metal of this series which has the desired fluorescence. It is usually either terbium ($Tb^{+3}$) or europium ($Eu^{+3}$). The glass slides are thus derivatized by one intercalating agent which serves to immobilize the analyte:analyte-specific moiety duplex while another intercalating agent, in solution, serves as the energy donor.

Any intercalating compounds can be used in this embodiment, as long as the pair used in the capture of the hybrid and as the energy donor have different excitation optima. Some intercalators which can be used in the capture of the hybrid are the psoralenamines, specifically, 8-[[[(diethylamino)methyl]propyl]oxy]psoralen, 5(N-piperadinyl)-8-methoxypsoralen, which is derivatized with linkers which contain secondary or tertiary amino groups or quartenary ammonium salts; phenanthridine dyes, such as ethidium bromide and 6-(-4'-carboxyphenyl)-3,8-diamine-5-methyl phenanthridinium chloride (M-B 3492).

Intercalators which can be used as energy donors include the acridine dyes, such as 9-aminoacridine, and the coumarins, for example, 7-hydroxy-4-methylcoumarin, 7-amino-4-methylcoumarin and 4-methyl-7-sulphato-methylcoumarin.

The preferred intercalator used in the capture of the hybrids is M-B 3492. The preferred energy transfer pair is the intercalator 9-aminoacridine as the donor and $Eu^{+3}$ as the acceptor.

The polynucleotide probes carrying the chelated metal label are prepared as described in Stavrianopoulos, U.S. Pat. No. 4,707,440 and assigned to the Instant assignee. The disclosure of this patent is herein incorporated by reference. As is more fully described therein, the chelator is attached to the polynucleotide sequence of the probe through a linkage group, or "linker arm", such that this attachment does not substantially interfere with the hybridization of the polynucleotide. The base moiety, to which it is preferably attached, can be a purine or pyrimidine. Preferred linkage groups include those having an allylamine moiety. Preferred chelators include diethylenetriamine pentaacetic acid (DTPA) and trans-diaminocyclohexane tetraacetic acid (DCTA).

In other embodiments of this Invention, the intercalator is not part of the energy transfer system, but comprises one or more fluorophores that act as either the energy donors or energy acceptors. The intercalator can be any substance, as long as it is different from the capture intercalator. Such an intercalator can be, for example, any one of the psoralenamines listed above and the energy donor, can be a naphthalene sulfonamide. M-B 3492 can also serve as an intercalator which comprises e.g., a pyrene compound that serves as the energy donor.

The fluorophores or the fluorescent energy compounds can be attached to the intercalator by any of a number of linkages or linker arms. Such linker arms are well known in the art and are described in Ward, U.S. Pat. No. 4,711,955 and in Stavrianopoulos, U.S. Pat. No. 4,707,440.

The fluorescent energy donor compound can also be a chelated lanthanide metal, when the probe is labeled with either a non-lanthanide fluorescent compound or is labeled with a lanthanide metal that is different from the metal which is serving as the energy donor.

Polynucleotide probes can also be labeled with fluorescent energy acceptor compounds that are not lanthanide metals. Such energy acceptors can be fluorescein, Texas Red, Rhodamine B and other fluorescent compounds. These compounds can be attached to polynucleotide probes via linkages, also well known in the art. See, e.g., Engelhardt et al., European Publication No. 0,285,057, published on Oct. 5, 1988 and assigned to the instant assignee. EP 0 285 057 is based upon the priority document, U.S. application Ser. No. 391,440, filed on Jun. 23, 1982, which was abandoned in favor of Ser. No. 07/674,352 (filed on Nov. 21, 1984), which in turn was abandoned in favor of Ser. No. 07/140,980 (filed on Jan. 5, 1988). Ser. No. 07/532,704 was filed on Jun. 4, 1990 as a divisional application of 07/140,980 and has since issued as U.S. Pat. No. 5,241,060 on Aug. 31, 1993. This publication is herein incorporated by reference.

Detection of hybrid formation is accomplished using a fluorometer, preferably a novel TRF fluorometer, which is more fully described in commonly assigned U.S. application Ser. No. 304,748, filed Jan. 31, 1989, which issued as U.S. Pat. No. 5,061,076 on Oct. 29, 1991, concurrently pending herewith, the disclosure of which is incorporated herein, by reference.

The following example illustrates but is not a limitation of the invention.

EXAMPLE 1

In this example, the first intercalator, the phenanthridine dye M-B 3492, is used to capture the double-stranded target-probe hybrid to the surface of the slide and a second intercalator, 9-aminoacridine, is used in solution as the energy donor.

Slide Preparation

The glass coverslip surface is simultaneously methylated and aminopropylated at a ratio of 1 aminopropyl group per 100 methyl groups as follows. Fifteen fused silica microscope coverslips (2.2 cm×2.2 cm×0.8 mm) are boiled in 5M nitric acid for two hours then dried at 105° C. for 24 hours. They are then heated (118+2° C.) overnight in a covered evaporating dish containing aminopropyltriethoxysilane (13 μl), methyltriethoxysilane (2.9 ml) and xylene(22.5 ml). The coverslips are then removed, washed twice with water (10 ml) and allowed to air dry at room temperature.

The glass surfaces are then nitrobenzylated as follows. Ten of the coverslips treated as described above are placed in methylenetrichloride (10 ml) containing triethylamine (10 ml). Then, p-nitrobenzylchloride (100 mg) is added, the mixture is heated to 60° C. and maintained at that temperature overnight. The coverslips are washed three times in methylenetrichloride (10 ml) and air dried.

The glass surfaces are then diazotized as follows. Five of the coverslips treated as described above are introduced into 10% sodium hydrosulfite in water (10 ml) and heated to 100° C. for 30 minutes. The solution is removed while still hot and the coverslips are washed three times in sodium acetate buffer (10 ml) and twice in deionized water (10 ml). The coverslips are then transferred to a tube containing $NaNO_2$ (25 g) in cold 2M HCl (10 ml). This tube is supported in a beaker (250 ml) of ice to maintain a temperature of 0° C. The beaker containing the tube is placed in a dessicator connected to a water aspirator and maintained at low pressure for 20 minutes. The coverslips are then washed three times with cold 0.15M acetic acid (10 ml) and stored immersed in this liquid at 4° C.

Next, 6-(4'-carboxyphenyl)-3,8-bromoacetylamidyl-5-methylphenanthridinium chloride, (III) is prepared as follows. A 100 mg portion of 6-(-4'-carboxyphenyl)-3,8-diamino- 5-methylphenanthridinium chloride (M-B 3492) (I) is dissolved in dimethylformamide (5 ml), 2.5M dimethylaminopyridine (7 ml) is added followed by addition of N-hydroxylsuccinimidyl ester of bromoacetic acid (II) (140 mg). The mixture is reacted for 10 minutes at room temperature to bromoacetylate the amino groups of (I), thereby forming compound III.

Formation of the tyramide of compound 111, is as follows. N-hydroxysuccinimide (33 mg) is dissolved in the reaction mixture prepared above by heating to 70° C., then dicyclohexylcarbodiimide (61 mg) is added. This is reacted at 70° C. for 90 minutes, an additional amount (6 mg) of the carbodiimide is added and the reaction is continued for another 30 minutes. The mixture is cooled to 0° C. and the precipitated dicyclohexylurea is settled by centrifugation. The supernatant, containing 6-(-4'-N-hydroxysuccinimidyl carboxy phenyl)-3,8-bis bromoacetamidyl-5-methylphenanthridinium chloride (IV) is recovered. A solution of tyramine [4-(2'-amino)ethylphenol] (1.0 g) in water (5 ml) is formed by bringing it to pH 7 by addition of concentrated HCl. This solution is added to the supernatant containing compound IV and reacted at room temperature for one hour. This mixture is then reduced to a red oil by evacuation at 60° C., and is then extracted with water to remove excess tyramine. Compound (VI) is then recrystalized from ethanol-acidified with HCl.

Azo coupling of the resulting intercalator to the activated glass surface is as follows. A glass coverslip derivatized as above, is transferred to cold (0° C.) 20 mM sodium phosphate buffer, pH 6.8 (1 ml) and the above dimethylformamide solution (5 ml), containing compound VI, is added. This mixture is reacted at 0° C. for one hour to form an azo linkage. The temperature is raised to room temperature overnight to hydrolyze the bromoacetyl groups. The light red coverslips are rinsed repeatedly with alcohol to remove uncoupled material and air dried.

Probe Preparation

The sequence of the probe prepared in accordance with this model experimental procedure is $(dT_3AAdU)_7$. A 5-hydroxy-DCTA is reacted with thiopropionic acid in a manner substantially identical with that described for the thiopropionic acid hydrazide in Example 3 of Stavrianopoulos, U.S. Pat. No. 4,707,440, supra. The disclosure of this patent is herein incorporated by reference.

Preparation of Sample for Assay

1) In a well of a four-well microscope slide, the sample is combined with, 2.0 M NaPO4 buffer, probe, distilled water and formamide to make a solution of 150 microliters total volume in which:
 a) pH is 6.5–7.0
 b) sodium ion concentration is 100 millimolar,
 c) $T_m$ of desired probe-target hybrid is 42° C.,
 d) probe concentration is 70 nM (phosphate).

2) The well is covered with derivatized fused silica coverslip, derivatized slide down and heated to 95° C. to denature double helical regions of target.

3) Hybridization is carried out for 5 minutes at approximately 6° C. below the $T_m$ (37° C. for $(dT_3AAdU)_7$) to form probe-target hybrids.

4) The sample is incubated at room temperature for five minutes to bind double-stranded DNA to coverslip by intercalation.

5) The solution is removed from the slide well and replaced with a wash buffer (as in step 1, except there is no probe). The sample is equilibrated at room temperature for 5 minutes.

6) The wash solution is removed. 100 microliters of solution 1.1 micromolar in energy donor and 150 millimolar in sodium phosphate (pH 6.8) is added and equilibrated for 5 minutes.

7) The coverslip is removed and excess solution is shaken off. The coverslip is mounted onto the sample delivery system.

Automated Assay

1) When using automated instrumentation in which a sample delivery system positions vessels, such as tubes or cuvettes, or analytical elements containing samples to be excited and to emit energy to be detected, the sample is automatically positioned for processing.

2) Step 1 above is repeated for each of the sample-containing analytical elements to be examined.

For example, in a TRF laser fluorometer:
a) laser pulses (337 nm nitrogen gas laser for psoralenamine energy donor, 405 nm diphenylstilbene dye laser for 9-aminoacridine energy donor).
b) photodiode detects laser pulse intensity; this is digitized and transferred to array in computer memory.
c) 200 microseconds after laser pulse, photon counting begins at 620 nm. Photons from sample are counted for 1.024 milliseconds.
d) Photon count is transferred to computer temporary storage.
e) 45 milliseconds after laser fires, photons from sample are counted for a further 1.024 milliseconds. This is the dark count.
f) Dark count is transferred to computer. Difference between count in temporary store and dark count is stored in a second array in memory.
g) After 50 milliseconds elapse, cycle restarts at a), above.

3) User chooses whether to have computer calculate the average photon count per second of photon counting time by averaging numbers in the second array; or to normalize the count to unit laser output by dividing each number in the second array by the corresponding number in the first array. The results are reported to the operator by computer. The computer also calculates and reports the confidence level of the result for that sample.

What is claimed is:

1. A nucleic acid hybridization composition comprising:
 an oligo- or polynucleotide having directly or indirectly bound thereto at least one lanthanide metal or at least one fluorophore, each acting as either an energy donor or an energy acceptor;
 a solid matrix having at least one surface to which is attached a first intercalator capable of capturing a double-stranded nucleic acid;
 a second intercalator, that may or may not comprise at least one fluorophore, said second intercalator or said fluorophore, each acting as either an energy donor or an energy acceptor wherein upon hybridization of said oligo- or polynucleotide to a complementary oligo- or polynucleotide, said energy donor and said energy acceptor are within proximate distance of each other such that energy from said energy donor is absorbed by said energy acceptor.

2. The composition of claim 1 wherein said proximate distance is equal to or less than Furster's radius.

3. The composition of claim 2 wherein said proximate distance is 30 Angstroms or less.

4. The composition of claim 1 wherein said lanthanide metal is selected from the group consisting of europium and terbium.

5. The composition of claim 1 wherein said lanthanide metal is chelated.

6. The composition of claim 5 wherein said chelator is selected from the group consisting of diethylenetriamine pentaacetic acid (DTPA) and transdiaminocyclohexane tetraacetic acid (DCTA).

7. The composition of claim 5 wherein said lanthanide chelate is bound to said oligo- or polynucleotide through a linkage group.

8. The composition of claim 7 wherein said linkage group comprises an allylamine moiety.

9. The composition of claim 8 wherein said allylamine moiety comprises allylamine.

10. The composition of claim 1 wherein said flurophore is selected from the group consisting of a naphthalene sulfonamide and a pyrene compound.

11. The composition of claim 1 wherein said first intercalator is bound to said surface through a linkage group.

12. The composition of claim 11 wherein said solid matrix comprises activated glass and said linkage group comprises an amino linkage group on said activated glass.

13. The composition of claim 12 wherein said linkage group terminates in a substituent capable of reacting with amino groups and said linkage group does not interfere with other components in the composition.

14. The composition of claim 1 wherein the double-stranded nucleic acid capturable by said first intercalator is selected from the group consisting of DNA, RNA and DNA-RNA hybrids.

15. The composition of claim 1 wherein said first intercalator is selected from the group consisting of phenanthridines and psoralenamines.

16. The composition of claim 15 wherein said phenanthridine comprises ethidium bromide.

17. The composition of claim 15 wherein said phenanthridine is 6-(4'-carboxyphenyl)-3,8-diamine-5-methyl phenanthridine chloride.

18. The composition of claim 15 wherein said psoralenamine is selected from the 8-[[[(diethylamino)methyl]propyl]oxy]psoralen and 5-(N-piperadinyl)-8-methoxypsoralen derivatized with linkers that contain secondary or tertiary amino groups or quaternary ammonium salts.

19. The composition of claim 1 wherein said second intercalator is selected from the group consisting of acridines and coumarins.

20. The composition of claim 19 wherein said acridine comprises 9-aminoacridine.

21. The composition of claim 19 wherein said coumarin is selected from the group consisting of 7-hydroxy-4-methylcoumarin, 7-amino-4-methylcoumarin and 4-methyl-7-sulphatomethoxycoumarin.

22. The composition of claim 1 wherein said first intercalator comprises 6-(4'-carboxyphenyl)-3,8-diamine-5-methyl phenanthridine chloride and said second intercalator comprises 9-aminoacridine.

23. The composition of claim 1 wherein said fluorophore in the second intercalator is selected from the group consisting of a chelated lanthanide metal, a naphthalene sulfonamide and a pyrene compound.

24. The composition of claim 1 wherein said first intercalator comprises 6-(4'-carboxyphenyl)-3,8-diamine-5-methyl phenanthridine chloride, said second intercalator comprises 9-aminoacridine and said lanthanide metal comprises europium.

25. A nucleic acid hybridization composition comprising:
an oligo- or polynucleotide having directly or indirectly bound thereto at least one lanthanide metal or at least one fluorophore, each acting as either an energy donor or an energy acceptor;
a solid matrix having at least one surface to which is attached (i) a first intercalator capable of capturing a double-stranded nucleic acid and acting as either an energy donor or an energy acceptor at a characteristic fluorescence emision; and (ii) a second intercalator that may or may not comprise at least one fluorophore, wherein said second intercalator is capable of capturing double-stranded nucleic acid, and wherein said second intercalator or said fluorophore acts as either an energy donor or an energy acceptor at a characteristic fluorescence emission which is different from the characteristic fluorescence emission of said first intercalator.

26. A nucleic acid hybridization assay process for detecting in a sample the presence of a nucleic acid sequence of interest, which process comprises:
(a) contacting a sample suspect of containing said nucleic acid sequence of interest with an oligo- or polynucleotide hybridizable therewith, said nucleic acid sequence of interest being present in single-stranded form or having been rendered at least partially single-stranded, and said oligo- or polynucleotide having directly or indirectly bound thereto a lanthanide metal or a fluorophore, each independently acting as either an energy donor or an energy acceptor;
(b) permitting hybridization of said nucleic acid sequence of interest and said oligo- or polynucleotide to form a complex;
(c) contacting said complex with:
(i) a solid matrix having at least one surface to which is attached a first intercalator capable of capturing double-stranded nucleic acid,
and (ii) a second intercalator with or without a fluorescent compound attached thereto, each independently acting as either an energy donor or an energy acceptor, the fluorescence emissions of said first and second intercalators being characterized by different wavelengths;
wherein upon hybridization of said oligo- or polynucleotide to said nucleic acid sequence of interest, said energy donor and said energy acceptor are within proximate distance of each other such that energy from said energy donor is absorbed by said energy acceptor; and
(d) detecting any energy emitted from said energy acceptor.

27. The process of claim 26 further comprising the step of separating any unhybridized oligo- or polynucleotide from any complex that is formed.

28. The process of claim 26 wherein said second intercalator is attached to said solid matrix.

29. The process of claim 26 wherein said second intercalator is in solution.

30. The process of claim 26 wherein said proximate distance is equal to or less than Furster's radius.

31. The process of claim 30 wherein said proximate distance is 30 Angstroms or less.

32. The process of claim 26 wherein said lanthanide metal is selected from the group consisting of europium and terbium.

33. The process of claim 26 wherein said lanthanide metal is chelated.

34. The process of claim 33 wherein said chelator is selected from the group consisting of diethylenetriamine pentaacetic acid (DTPA) and transdiaminocyclohexane tetraacetic acid (DCTA).

35. The process of claim 33 wherein said lanthanide chelate is bound to said oligo- or polynucleotide through a linkage group.

36. The process of claim 35 wherein said linkage group comprises an allylamine moiety.

37. The process of claim 36 wherein said allylamine moiety comprises allylamine.

38. The process of claim 26 wherein said flurophore is selected from the group consisting of a naphthalene sulfonamide and a pyrene compound.

39. The process of claim 26 wherein said surface comprises activated glass and said first intercalator is attached thereto through an amino functionality on said surface.

40. The process of claim 39 wherein said first intercalator is bound to said surface through a linkage group.

41. The process of claim 40 wherein said linkage group terminates in a substituent capable of reacting with amino groups and said linkage group does not interfere with other components in the composition.

42. The process of 26 wherein the double-stranded nucleic acid capturable by said first intercalator is selected from the group consisting of double-stranded DNA, double-stranded RNA and DNA-RNA hybrids.

43. The process of claim 26 wherein said first intercalator is selected from the group consisting of phenanthridines and psoralenamines.

44. The process of claim 43 wherein said phenanthridine comprises ethidium bromide.

45. The process of claim 43 wherein said phenanthridine is 6-(4'-carboxyphenyl)-3,8-diamine-5-methyl phenanthridine chloride.

46. The process of claim 43 wherein said psoralenamine is selected from the group cons8-[[[(diethylamino)methyl] propyl]oxy]psoralen and 5-(N-piperadinyl)-8-methoxypsoralen derivatized with linkers that contain secondary or tertiary amino groups or quaternary ammonium salts.

47. The process of claim 26 wherein said second intercalator is selected from the group consisting of acridines and coumarins.

48. The process of claim 47 wherein said acridine comprises 9-aminoacridine.

49. The process of claim 47 wherein said coumarin is selected from the group consisting of 7-hydroxy-4-methylcoumarin, 7-amino-4-methylcoumarin and 4-methyl-7-sulphatomethoxycoumarin.

50. The process of claim 26 wherein said first intercalator comprises 6-(4'-carboxyphenyl)-3,8-diamine-5-methyl phenanthridine chloride and said second intercalator comprises 9-aminoacridine.

51. The process of claim 26 wherein said fluorophore in the second intercalator is selected from the group consisting of a chelated lanthanide metal, a naphthalene sulfonamide and a pyrene compound.

52. The process of claim 26 wherein said first intercalator comprises 6-(4'-carboxyphenyl)-3,8-diamine-5-methyl phenanthridine chloride, said second intercalator comprises 9-aminoacridine and said lanthanide metal comprises europium.

53. A nucleic acid hybridization assay kit comprising, in packaged combination, reagents for detecting in a sample the presence of a nucleic acid sequence of interest, including the following:

a first container having therein a plurality of solid matrices having bound to at least one surface thereof a first intercalator capable of capturing double-stranded nucleic acid;

a second container having therein an oligo- or polynucleotide hybridizable with said nucleic acid sequence and having directly or indirectly bound thereto at least one lanthanide metal or at least one fluorophore each acting as either an energy donor or an energy acceptor; and at least one additional container having therein a second intercalator with or without at least one fluorophore attached thereto, each acting as either an energy donor or an energy acceptor, wherein the fluorescence emissions of said first and second intercalators are characterized by different wavelengths.

* * * * *